United States Patent [19]

Rerkasem

[11] Patent Number: 6,066,785

[45] Date of Patent: May 23, 2000

[54] METHOD FOR PRODUCING HYBRID PLANTS USING FERTILITY SELECTIVE GROWTH MEDIA

[75] Inventor: Benjavan Rerkasem, Chaing Mai Province, Thailand

[73] Assignee: Chiang Mai University, Chiang Mai Province, Thailand

[21] Appl. No.: 08/994,969

[22] Filed: Dec. 19, 1997

Related U.S. Application Data

[63] Continuation-in-part of application No. PCT/US96/10525, Jun. 14, 1996.
[60] Provisional application No. 60/036,582, Apr. 10, 1997.

[30] Foreign Application Priority Data

Jun. 20, 1995 [AU] Australia ............................... PN3642

[51] Int. Cl.⁷ .............................. A01H 5/00; A01H 5/10; A01H 1/00
[52] U.S. Cl. ........................ 800/320; 800/260; 800/265; 800/266; 800/269; 271/275; 271/295; 271/298; 271/320.1; 271/320.2; 271/320.3
[58] Field of Search ............................... 47/58; 800/274, 800/260, 303, 320.3, 265, 266, 269, 271, 275, 295, 298, 320, 320.1, 320.2

[56] References Cited

U.S. PATENT DOCUMENTS

| | | |
|---|---|---|
| 4,028,084 | 6/1977 | McNulty et al. . |
| 4,047,930 | 9/1977 | Kerr . |
| 4,925,477 | 5/1990 | McDaniel . |

FOREIGN PATENT DOCUMENTS

WO 97/00602  9/1997  WIPO .

OTHER PUBLICATIONS

S. Jamjod et al., "Combining ability of the response to boron deficiency in wheat," 1993, pp. 359–361.
S.C. Agarwala, et al., "Pollen development in maize plants subjected to molybdenum deficiency," 1979, pp. 1946–1950.
Frankel et al., "Pollination Mechanisms, Reproduction and Plant Breeding," Auxins and Related Compounds, 1977, pp. 135–137.
Tak–Cheung Lau et al., "Effects of Soil Nitrogen on Pollen Production, Pollen Grain Size, and Pollen Performance In Cucurbita Pepo," 1993, American Journal of Botany, vol. 80(7): pp. 763–768.
B. Rerkasem et al., "Grain set failure in boron deficient wheat," 1993, Plant and Soil, pp. 309–312.
Rupinder J.K. Sidhu et al., "Metabolic Role of Boron in Germinating Pollen and Growing Pollen Tubes," 1986, Biotechnology and Ecology of Pollen Proceedings, pp. 373–378.
Graham, R.D., "Male sterility in wheat plants deficient in copper," 1975, Nature vol. 254, pp. 514–515.
Rerkasem Benjavan, "Grain Set Failure and Boron Deficiency in Wheat in Thailand," 1989, Journal of Agriculture 5,1: pp. 1–10.
Jensen, N.F., "Plant Breeding Methods," 1988, Agronomy Journal, vol. 44, No. 1, pp. 169–202.
Rerkasem, Benjavan, "Boron Deficiency in Sunflower and Green Gram at Chiang Mai," 1986, Journal of Agriculture 2, 2: pp. 163–172.
Rerkasem, Benjavan, "Boron Deficiency in Two Wheat Genotypes in a Warm, Subtropical Region," 1994, pp. 887–890.
C. Cheng et al., "Effects of Boron on Pollen Viability in Wheat," 1993, Plant and Soil, vol. 155/156, pp. 313–315.
P.N. Sharma et al., "Zinc Deficiency and Pollen Fertility in Maize," 1990, Plant and Soil, 124, pp. 221–225.
Graham, Robin D., "Selecting Zinc–efficient Cereal Genotypes for Soils of Low Zinc Status," 1992, Plant and Soil, vol. 146, pp. 241–250.
Hartwig, E.E., "Identification and Inheritance of Inefficient Zinc Absorption in Soybean," 1991, Crop. Sci., vol 31, pp. 61–63.
Graham, Robin D., "The Sensitivity of Hexaploid and Octoploid Triticales and their Parent Species to Copper Deficiency," 1979, Aus. J. Agric. Res., vol. 30, pp. 791–799.
Allard, R.W., "Principles of Plant Breeding," 1960, John Wiley & Sons, Inc., pp. 218–223.
Sharma, C.P. et al., "Manganese Deficiency in Maize Affects Pollen Viability," 1991, Plant and Soil, vol. 138, pp. 139–142.
L.W. Briggle, "A Recessive Gene for Male Sterility in Hexaploid Wheat," 1970, Crop Science, vol. 10, pp. 693–696.

(List continued on next page.)

*Primary Examiner*—Lynette R. F. Smith
*Assistant Examiner*—Ousama M-Faiz Zaghmout
*Attorney, Agent, or Firm*—Michael A. Gollin; Venable

[57] ABSTRACT

A method of producing hybrid plants involves inducing cross-pollination of self-pollinating species by selecting a female plant and a male plant having different genotypes, the female plant having a phenotype of sensitivity to a micronutrient deficiency, and the male plant having a phenotype of male fertility, growing the female plant to sexual maturity in a fertility-selective growth medium deficient for the micronutrient, to produce a plant having female fertility and male sterility, growing the male plant to sexual maturity to produce a plant having high male fertility, cross-pollinating the female plant with pollen from the male plant to produce cross-fertilization with essentially no self-fertilization, raising the female plant to produce hybrid seeds having genetic material from both parents, and harvesting the hybrid seeds. Fertility selective media can be identified by using a set of check genotypes with known responses to a micronutrient deficiency, choosing as the fertility-selective medium those that give desired differences in male sterility between the standard checks. The plants may be wheat and the growth medium may be deficient for boron. The method preferably comprises determining a correlation between boron content of the male reproductive organs by chemical analysis and observation of degrees of male sterility.

29 Claims, 3 Drawing Sheets

OTHER PUBLICATIONS

Driscoll, C.J., "X Y Z System of Producing Hybrid Wheat," 1972, Dept. Of Agronomy and Range Science, pp. 516–517.

Rerkasem, Benjavan, "Correcting Boron Deficiency Induced Ear Sterility in Wheat and Barley," 1989, Thai Journal, Soils and Fertilizers pp. 200–209.

Lu, X.G. et al., "Current Status of Two–Line Method of Hybrid Rice Breeding," 1994, Int'l Rice Research Institute, pp. 37–49.

Yuan, L.P. et al., "Status of Hybrid Rice Research and Development," pp. 8–24.

Lucken, K.A. et al., "Hybrid Wheat Status and Outlook," 1988, Int'l Rice Research Institute, pp. 243–255.

Nambiar, E.K.S., "Genetic Differences in the Copper Nutrition of Cereals. I Differential Responses of Genotypes to Copper," 1976, Aust. J. Agric. Res., vol. 27, pp. 453–463.

Mackill, D.J. et al., "Public Sector Research on Hybrid Rice in the United States," 1994, Int'l Rice Research Institute, pp. 235–239.

Craig, William F., "Production of Hybrid Corn Seed," 1977, American Society of Agronomy, Inc., No. 18, pp. 671 and 686–693.

Lin, Justin Yifu et al., "Economic Assessment of the Potential for Hybrid Rice in Tropical Asia: Lessons from the Chinese Experience," Crop Sci., pp. 131–141.

Rerkasem, K. et al., "Wheat for the Nontraditional Warm Areas," Proceedings of the International Conference, 1990, pp. 500–504.

Jensen, Neal F., "Genetic Male Sterility," John Wiley & Sons, 1998, pp. 235–241.

E.G. Heyne et al., "Wheat Breeding," American Society of Agronomy, Inc., 1967, pp. 269 and 281–283, 302–306.

Rerkasem, "Boron Deficiency in Wheat," Multiple Cropping Center, 1992, Report No. 1, pp. 126–128.

"Can Grain Yields Keep Pace?" Science News, vol. 152, 1997, pp. 104–105.

Galrao et al. Rev. Bras. Cienc. Solo. 1988. vol. 12: 147–152.

Poehlman. Breeding field crops. 1986. AVI.Text.

METHOD FOR PRODUCING HYBRID PLANTS USING FERTILITY SELECTIVE GROWTH MEDIA

This application is a continuation-in-part of international patent application PCT/US96/10525, filed Jun. 14, 1996, the United States being designated, and claims the benefit of U.S. provisional patent application 60/036,582, filed Apr. 10, 1997, both of which are hereby incorporated by reference in their entirety.

BACKGROUND OF THE INVENTION

This invention provides a simple and economical method for producing hybrid seeds by controlling micronutrient content of the male reproductive organs. More specifically, the invention relates to a method for inducing cross-pollination in plant species such as wheat that are normally self-pollinating, by selecting parents having differential fertility when grown in micronutrient-deficient growth media, and crossing them.

Hybrid seeds, those which are genetically heterozygous, have many advantages over homozygous seeds. Hybrid plants commonly grow faster, achieve higher biomass and yield, and have greater disease resistance than their better parent. This phenomenon is known as heterosis.

Plant hybridization is a crowded and mature art, but there has long been a need for effective, simple, economical methods for breeding hybrid wheat and other small-grained self-fertilizing plants. Hybrids are made by inter-crossing separate inbred lines. Generally, a breeder introduces viable donor pollen from a male fertile line onto the potentially fertile stigmas of a male sterile line that lacks fertile pollen. Genetic, mechanical, chemical, and biotechnological processes have been used to induce male sterility to facilitate hybrid seed production.

Genic male sterility has been found in barley. (Suneson, C. A., "A male sterile character in barley," *J. Heredity.* 31:213–214 (1940)), and wheat (Suneson, C. A., "Use of Pugsley s sterile wheat in cross breeding," *Crop Sci.* 2:534–535 (1962)). However, since plants with the male sterile genotype are self-infertile, they (and hence the male sterile genes) can only be maintained in heterozygous populations. E.g. see Briggle, L. W., "A recessive gene for male sterility in hexaploid wheat," *Crop Sci.* 10:693–696 (1970); Gill, B. S. and Anand, S. C., "Genetic male sterility for hybrid seed production in wheat," *Crop Sci.* 10:385–386 (1970). This has made it necessary to develop complicated breeding procedures to make use of genic male sterility. E.g. Suneson, C. A., "The use of male-sterility in barley improvement," *J. Am. Soc. Agron.* 37:72–73 (1945); Driscoll, C. J., "X Y Z system of producing hybrid wheat," *Crop Sci.* 12:516–517 (1972); and "Modified X Y Z system of producing hybrid wheat," *Crop Sci.* 25:1115–1116 (1985).

Cytoplasmic-genetic male sterility and fertility restoration requires breeding a male sterile line which retains female-fertile characteristics. Allard, R. W. *Principles of Plant Breeding* (John Wiley & Sons 1960), pp. 243–251. A plant that is considered to have desirable characteristics and is to be the female parent needs to go through extensive inbreeding through many generations over as many as ten years to be made male sterile. In the process of producing hybrids two other breeding programs have to be running concurrently. One is required to restore the fertility of the male sterile line when the hybrid is growing, so that it can be raised for further hybridization. The other is to introduce the male sterile gene or male sterile cytoplasm. The sources of male-sterility and the restorers are often unreliable. The method of using cytoplasmic genetic male sterility and fertility restoration systems was developed to produce hybrid rice seeds in bulk in China. (Yuan and Virmani, 1988). It has also been used for alfalfa. U.S. Pat. No. 3,570,181. Another type of genetic pollination control is nuclear genic male sterility. This has been proposed to develop hybrid wheat parents. Lucken, K. A. and Johnson, K. D., "Hybrid wheat status and outlook" in *Hybrid Rice* (International Rice Research Institute 1988), pp. 243–255. In another approach, environment-sensitive genic male sterile rice lines are sterile under certain daylength and temperature conditions, but fertile under other conditions. Lu et al., "Current status of two-line method of hybrid rice breeding," *Hybrid Rice Technology* (IRRI 1994), pp. 37–49. These may be used in a two-line breeding method, but it is difficult to control growing conditions suitably to provide the desired degree of fertility or sterility.

The mechanical approach involves manual emasculation of floral structures. The male part is removed manually, and then the female part of the flower is cross-fertilized with pollen (male gametes) from another plant. This approach is feasible in plants with large flowers with male and female parts located separately such as corn, but many important agricultural plants such as wheat and rice have very small flowers in which the male and female parts are located very close together. The mechanical approach is labor intensive, time-consuming, and inefficient, limiting the number of flowers that can be manually cross-fertilized and the number of crosses made. It has been impossible to explore the characteristics and advantages of many gene combinations due to these limitations.

Chemical approaches have been employed in which a gametocidal composition is applied to the anthers of a plant to induce sterility of the male organ. The gametocidal composition may comprise cinnoline compounds (EP 363236, U.S. Pat. No. 5,129,939), azetidine derivatives (EP 29265, U.S. Pat. No. 4,555,260), polychloroacetic acids and their derivatives (SU 641926), amega-amino-carboxylic acids (SU 635929), tetra-chloroalkane derivatives (SU 635928), and the like. However, chemical approaches are often costly and may produce undesirable side effects, for example retardation of plant growth, and poor seed set. Furthermore, chemical hybridizing agents have significant negative environmental impacts and so some countries have banned them.

Recombinant DNA technology has also been developed to produce male sterile plants. For example Albertsen et al. (AU 9337990) disclose a method of providing heritable, externally-controllable male-sterility in a plant, by inactivating a flavonol-producing gene. In another application (EP 513884), a method of inducing male-sterility by inhibiting the expression of a gene encoding an enzyme in chalcone biosynthesis is reported. There are several problems associated with these approaches, including the restriction of such technology to readily-transformable crop species, the time taken to obtain transgenic crops and the small scale of operations relating to recombinant DNA technologies. Furthermore, the present state of the art can only address one or two specific problems at a time. Approaches utilizing traditional plant breeding have the same limitations and require many generations of back-crossing to remove undesirable traits.

A significant disadvantage of these prior approaches to producing hybrid seeds is their high cost. Thus, efforts to hybridize wheat and other small grained self-fertilizing plants simply, effectively, and economically have failed, and there is a need for an economical method for mass-producing hybrid wheat and rice and similar plants.

In a different field of study, it was reported long ago that copper deficiencies can cause male sterility in wheat but this observation did not lead to any viable method for hybridizing wheat. Graham, R. D., "Male sterility in wheat plants deficient in copper," *Nature* 254:514–515 (1975). Deficiencies of other micronutrients have been found to cause male sterility in other plant species, including manganese, zinc and molybdenum deficiency in corn. C. P. Sharma, P. N. Sharma, C. Chatterjee, and S. C. Agarwalla, "Manganese deficiency in maize affects pollen viability," Plant and Soil, 138:139–142 (1991); P. N. Sharma, C. Chatterjee, S. C. Agarwalla, and C. P. Sharma, "Zinc Deficiency and pollen fertility in maize (*Zae mays*)", Plant and Soil, 124:221–225 (1990); S. C. Agarwalla, C. Chatterjee, P. N. Sharma, C. P. Sharma, and N. Nautiyal, "Pollen development in maize plants subjected to molybdenum deficiency," Can. J. Bot., 57:1946–1950.

Boron-deficient soils occur naturally throughout the world. Soil boron may be depleted by repeated cropping. Liming, a routine soil amendment in agriculture, can also decrease the amount of boron that is available to plants. Research in this area has been directed toward understanding the interaction of boron deficiency and environmental factors such as temperature, humidity, and light. Efforts have also been made to diagnose the mechanisms of sterility, to find crops that can grow well and develop viable pollen in boron-deficient soil, and to restore fertility by applying boron. Rerkasem, B., Netsangtip, R., Lordkaew, S., Cheng, C., "Grain set failure in boron deficient wheat," *Plant and Soil* 155/156:309–312 (1993); Cheng, C. and Rerkasem, B., "Effects of boron on pollen viability in wheat," *Plant and Soil* 155/156:313–315 (1993).

Genotypic differences in the response to micronutrient deficiency have also been reported in different species. This research is directed toward finding plants that are growth and yield tolerant of the deficiency, or to understanding the underlying biochemistry of fertility. For example, for copper deficiency in wheat, rye and triticale, see E. K. S. Nambiar, "Genetic differences in the copper nutrition of cereals. I. Differential response of genotypes to copper," Aust. J. Agric. Res., 27:453–463 (1976); R. D. Graham, and D. T. Pearce, "The sensitivity of hexaploid and octaploid triticales and their parent species to copper deficiency", Aust. J. Agric. Res., 30:791–799 (1979); and Marschner (1992). For manganese deficiency in barley, see W. Ralph, "Managing manganese deficiency," Rural Research, 130:18–22 (1986); and N. E. Marcar, and R. D. Graham, "Genotypic variation for manganese deficiency in wheat," J. Plant Nutrition, 10:2049–2055 (1987). For zinc deficiency in wheat, see R. D. Graham, J. S. Ascher and S. C. Hynes, "Selecting zinc-efficient cereal genotypes for soils of low zinc status," Plant and Soil, 146:241–250 (1992). For zinc deficiency in soybean, see E. E. Hartwig, W. F. Jones, T. C. Kilen, "Identification and inheritance of inefficient zinc absorption in soybean," Crop Sci., 31:61–63 (1991).

Likewise, the effects of boron deficiency on fertility in wheat and barley vary among genotypes. Rerkasem, B. and Jamjod, S., "Correcting boron deficiency induced ear sterility in wheat and barley," *Thai Jour. Soils and Fertilizers* 11:200–209 (1989). For example, when raised in medium having a low boron level, wheat line SW41 was self-infertile when bagged. Also, it was found that a wheat line raised in boron deficient medium had marginal fertility even when manually cross-fertilized by pollen from a fertile male. Rerkasem et al., *Plant and Soil* 155/156:309–312 (1993).

Male plant sterility induced by micronutrient deficiency has been viewed as a major disadvantage and an undesirable trait reducing the productivity of crops. There has been no suggestion of how to use this undesirable phenomenon in a productive fashion. In particular, past research does not suggest using micronutrient deficiency to provide a fertility-selective growth medium, and a method of selecting a female line which is micronutrient deficiency tolerant as to female fertility and micronutrient deficiency sensitive as to male fertility, and a male line that is micronutrient deficiency tolerant as to male fertility, and allowing cross-fertilization to occur between them. Most specifically, past research has not suggested a simple method to produce hybrids of small grains at field scale, thus lowering the cost of production and making hybrid seeds cost-effective for small grains.

The mechanisms for fertility differences are not known. The degree of male sterility in a plant is not indicated by boron concentrations in the soil, or in leaves and whole flowers (Rerkasem B. and S. Lordkaew, "Predicting grain set failure with tissue boron analysis," in Mann C. E and B. Rerkasem (eds.), *Boron Deficiency in Wheat.* pp. 9–14, CIMMYT Wheat Special Report No. 11. CIMMYT, Mexico, 1992; Rerkasem and Loneragan, 1994). At the general level, boron uptake, movement and transportation into a plant can be controlled by methods known to those familiar with the science of plant nutrition (Marschner, H., "Mineral Nutrition of Higher Plants," Academic Press, transportation into a plant can be controlled by methods known to those familiar with the science of plant nutrition (Marschner, H., "Mineral Nutrition of Higher Plants," Academic Press, London, 1995; Mortvedt, J. J., F. R. Cox, L. M. Shuman, R. M. Welch, eds. *"Micronutrients in Agriculture,"* Soil Sci. Soc. Amer. Book Series No. 4, SSSA, Madison, Wis., 1991). However, the possibility of using boron levels for precise control of male fertility/sterility was not previously recognized and was not accomplished prior to this invention.

SUMMARY OF THE INVENTION

An advantage of this invention is that it provides simple, effective, and economical methods for hybridizing wheat and other small-grained self-fertilizing plants. The invention takes advantage of the phenomenon of micronutrient deficiency-induced sterility as a means for hybridization, by controlling the micronutrient concentration available to the plant at different times in its life cycle, and selecting appropriate plant lines that are tolerant or sensitive to the micronutrient deficiency.

According to the invention, plants having a phenotype of male sterility inducible by micronutrient deficiency are used for breeding hybrids. This approach avoids the problems of the prior art, such as phyotoxicity, harmful effects on female fertility or toxic effects in the environment, and takes advantage of what is generally considered a productivity disadvantage of such plant lines.

The invention provides a method for producing hybrid seeds comprising:

(a) selecting from a plant species that is normally self-pollinating parents consisting of a female plant and a male plant having different genotypes, the female plant having a phenotype of male fertility sensitivity and female fertility tolerance to a micronutrient deficiency, such that the plant does not produce viable pollen but has fertile female parts; and the male plant having a phenotype of male fertility tolerance to the micronutrient deficiency, (b) growing the female plant to sexual maturity in a fertility-selective growth medium deficient for the micronutrient, to produce a plant having a phenotype of female fertility and male sterility, (c) growing the male plant to sexual maturity to produce a plant having a phenotype of high male fertility, (d) cross-pollinating the female plant with mature pollen from the male plant to produce cross-fertilization with essentially no self-fertilization, (e) raising the female plant to produce hybrid seeds having genetic material from both parents, and (f) harvesting the hybrid seeds.

Preferably, the female and male plants are different inbred lines selected from the group consisting of wheat, rice, barley, rye, triticale, maize, sunflowers, sorghum, oats, and millet. The growth medium may be soil, sand, vermiculite, or other appropriate material. The deficient micronutrient is preferably boron, but may be iron, manganese, copper, zinc, or molybdenum. The fertility-selective growth medium may be made deficient in the micronutrient by sequestering the micronutrient, preferably by liming the growth medium.

The fertility-selective growth medium is identified with the aid of standard check genotypes with male sterility responses, which may be known from the literature or determined empirically. Thus, a first step according to the invention involves identifying the fertility selective media by growing a set of standard check genotypes with known response to the micronutrient deficiency in a range of availability of the micronutrient from almost nil (e.g. 0.0001–0.001 micromolar) to sufficiency, and selecting as the fertility selective media those that give expected difference in male sterility responses among the standard checks. To identify a standard check genotype empirically, one screens a variety of genotypes at a low micronutrient level to determine which are male fertile and which are male sterile-female fertile.

The male and female are preferably raised in the same growth medium, but they may be raised in different growth media having different levels of the micronutrient. Cross-pollination occurs naturally by wind or insects according to the invention without manual pollen transport or other extensive assistance (although shaking the plants may be appropriate).

An embodiment of the invention further comprises the step of stimulating the fertility of the female plant before pollination by supplying the micronutrient to promote pollen gamete germination, without affecting male fertility of the female plant. The stimulating step preferably comprises applying the micronutrient directly to the female plant, or it may involve placing the female plant in a growth medium that is not deficient in the micronutrient.

A hybrid plant may be raised from the hybrid seed produced according to the invention. This plant may be subjected to any other manipulations known to those of skill in plant breeding, such as cloning, genetic recombination, or further breeding. The hybrid plant may then be reselected in the fertility-selective medium as to its male sterility/fertility to determine its potential as a female or male parent in further crosses. The hybrid F1 may then be crossed with a plant having a different genotype to produce a three-way cross, double-cross (four-way), or other crosses, for example:

male sterile F1 X male fertile F1→double cross hybrid
male sterile F1 X male fertile homozygous line→three-way cross hybrid
male sterile homozygous line X male fertile F1→three-way cross hybrid.

The hybrid plant preferably has a phenotype of male sterility when grown in a micronutrient-deficient environment, and the further crossing step comprises crossing the hybrid with a male plant having a different genotype. Alternatively, the hybrid plant may be male fertile, and the further crossing step may comprise crossing the hybrid with a female-fertile plant having a different genotype. The three-way cross or double-cross hybrid plant may be crossed again with a plant having a different genotype to produce a further cross.

Preferably, the plants are wheat and the micronutrient is boron. The fertility selective growth medium is identified by growing a set of standard check genotypes with known male fertility responses to boron deficiency in a range of boron availability, from almost nil to sufficiency. The standard check genotypes should have Grain Set Index (GSI) of 85–100% at sufficiency, and the fertility selective medium is chosen as the one that gives differences among the standard checks that are largest or at any predetermined levels. The standard check genotypes may be Fang 60, Sonora 64, SW41, BL1022, Tatiara, Gamneya or any whose male sterility responses to boron have been published, or they can identified empirically. In a light sandy loam a fertility selective growth medium was identified as having below 0.14 mg B/kg growth medium, most preferably below 0.09 mg B/kg, and even more preferably when lime was applied to this soil at the rate of 2 tons/ha. Liming does not change the B content but does reduce its bioavailability. Foliar sprays optionally applied to female fertile plants before pollination preferably have about 0.005 to about 0.01% boron, w/v, in solution.

In a preferred embodiment of the invention, precise control of male fertility/sterility may be provided by controlling the level of boron in the male reproductive organs, and the precise control of the level of boron in the male reproductive organs may be provided by the choice of plants with certain genotypes giving them capacity to transport appropriate amounts of boron into their male reproductive organs. Choosing plants of specific genotypes for variously desired characteristics is an art generally known to those who are skilled in plant breeding.

The level of male sterility/fertility is determined by the concentration of boron in the male reproductive organs; a relationship that is normally positively correlated. The precise level of boron in the male reproductive organs that gives a certain level of male sterility/fertility can be determined for any plant by experimentation. This may be done by growing plants in environments designed to vary, by known methods, the level of boron taken up from the rooting media, which can be soil or manmade, into the plant. The boron content of the male reproductive organs and level of male fertility are assessed and correlated, and thus any desired level of male fertility may be predetermined from the level of boron in the male reproductive organs.

In this embodiment, the method of producing a hybrid plant comprises (a) choosing as parents plants having different genotypes and each with a different predetermined ability to transport a desired level of boron into their male reproductive organs, (b) controlling male fertility/sterility in the parent by controlling the level of boron in the male reproductive organs, and (c) crossing the parent with a plant having a different genotype to produce a hybrid.

Preferably, the parent plants and boron levels are selected to produce male sterility in the female parent and male fertility in the male parent.

The method preferably comprises determining a correlation between boron content of the male reproductive organs by chemical analysis and observation of degrees of male sterility. The plant is preferably a cereal, and may be wheat, rice, barley, maize, triticale, sorghum, cotton, soybean, canola, broadbean or peas. Most preferably, the plant is wheat.

With some plant genotypes, the method provides that male fertility may be achieved by boron concentration in the anthers of about 11 mg B kg$^{-1}$ dry weight or more, and male sterility may be achieved by boron concentration in the anthers at about 10 mg B kg$^{-1}$ dry weight or lower, with the level of male sterility increasing with decreasing level of boron in the anthers.

With other plant genotypes, about 50% male sterility, with Grain Set Index about 50% when self-fertilised, may be achieved by boron concentration in the anthers at about 8 mg B kg$^{-1}$ dry weight or lower. Complete male sterility, Grain Set Index about 0% when self-fertilised, may be achieved by boron concentration in the anthers at about 6 mg B kg$^{-1}$ dry weight or lower.

The wheat plant preferably has a genotype that enables it to maintain a level of boron in the anthers at 11 mg B kg$^{-1}$ dry weight or more which confer complete male fertility, Grain Set Index 100% when self-fertilised. The wheat plant may have a genotype that enables it to maintain a level of boron in the anthers at 10 mg B kg$^{-1}$ dry weight or less which confer male sterility, with Grain Set Index when self-fertilised <85% and decreasing with decreasing boron level in the anthers.

The wheat plant may have a genotype that enables it to maintain a level of boron in the anthers at about 8 mg B kg$^{-1}$ dry weight or less which confer male fertility/sterility ratio at about 50:50, with Grain Set Index when self-fertilised about 50% or lower. The wheat plant may have a genotype that enables it to maintain a level of boron in the anthers at about 6 mg B kg$^{-1}$ dry weight or less which confer complete male sterility, with Grain Set Index when self-fertilised about 0%.

Preferably, the wheat genotype is selected from Fang 60 and others with similar boron uptake and transportation characteristics, or is selected from Gamenya, Tatiara, Kite, Machete, Spear, Bonza, Eradu, Warrigal, Wilgoyne, SW41 and others with similar ability to take up and transport low levels of boron into their male reproductive organs.

BRIEF DESCRIPTION OF THE DRAWINGS

The invention is better understood by reading the following detailed description with reference to the accompanying figures.

FIG. 1 illustrates the wheat flower, with normal and male sterile phenotypes resulting from boron deficiency.

FIG. 1E is male fertile, with yellow anthers 2–3 mm long, with 2000–3000 pollen grains each, held above the stigma on extended filaments. When self fertilized, this phenotype will have 90–100% grain set. Florets represented by FIGS. 1F, 1G, and 1H have essentially no grains.

FIG. 1F is male sterile, with smaller shriveled anthers; pollen grains are fewer, misshapen like deflated footballs, about half normal size, and do not stain with iodine.

FIG. 1G is male sterile, with anthers less than 0.5 mm, arrow shaped; filaments not extended; pollen grains are few (<100/anther), half normal size, empty, and do not stain with iodine.

FIG. 1H is male sterile, with anthers that appear as fine short hairs almost invisible to the naked eye.

FIG. 2 illustrates two examples of the layout and proximity of plants for cross-pollination according to the invention, as in Example 8.

DETAILED DESCRIPTION OF THE PREFERRED EMBODIMENTS

Figure 1A:
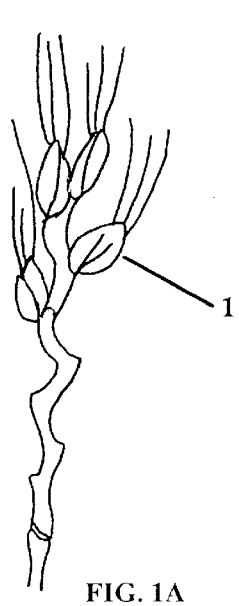
FIG. 1A shows a wheat ear with spikelets 1 and basal spikelets removed.
Figure 1B:
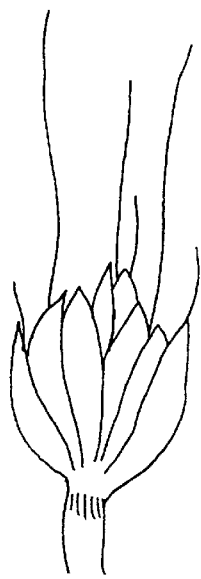
FIG. 1B shows a side view of a spikelet 1.
Figure 1C:
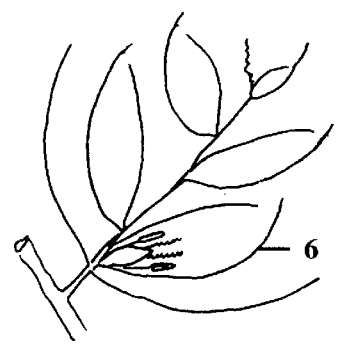
FIG. 1C shows a schematic of a spikelet with five florets within glumes 6; some internal detail is shown for the first floret from the base.
Figure 1D:
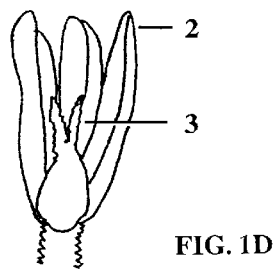
FIG. 1D depicts a floret before anthesis with glumes 6 removed to show anthers 1 at full size (about 2–3 mm), partly developed style and beginning of stigma 3 visible.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

According to the invention, the availability of a micronutrient to the plant at various critical times in the life cycle may be controlled to provide a desirable phenotypic effect of male fertility, or male sterility/female fertility. The important variables are as follows.

First, the fertility selective growth medium is identified by growing a set of standard check genotypes with known male fertility responses to the micronutrient deficiency in a range of availability from almost nil (0.0001 to 0.001 micromolar) to sufficiency. Sufficiency is known for all major agricultural crops and micronutrients. In general, almost nil means in the range of about 0.001 to about 0.2 micromolar in nutrient solutions added to man-made growth media, for most micronutrients, except molybdenum for which the minimum is about 0.00001 micromolar. In practice, the lowest achievable level is generally almost nil, because there are generally background impurities in water or salts which will permit plant viability without knowledge of their presence. Materials are available to strip out all amounts of a micronutrients leaving essentially, nil but at this level most plants simply will not grow.

The standard check genotypes should all have Grain Set Index (GSI) of 85–100% at sufficiency, and the fertility selective medium is chosen as the one that gives differences in male sterility among the standard checks that are largest or at predetermined levels. The standard check genotypes for wheat and boron may be Fang 60, Sonora 64 (tolerant), SW41, BL1022, Tatiara, Gamneya (sensitive), or any whose male sterility responses to boron have been published. For wheat and copper they may be Chinese Spring (tolerant), Halberd (moderate), or Gabo (sensitive), as well as other genetically close species such as rye (in general, tolerant) or triticale (tolerant, e.g. variety Beagle). Nambiar (1976); and Graham and Pearce (1979).

For barley and manganese, the standard check genotypes may be Weeah (tolerant) and Galleon (sensitive). Ralph (1986); and Marcar and Graham (1987). For wheat and zinc the standard check genotypes may be Excalibur, Schombergk, Warigal (tolerant) and Durati and Kamilaroi (sensitive). Graham, Ascher and Hynes (1992). For zinc and soybean they may be D77-6056 and Forrest (tolerant) and D82-3298 (sensitive). Hartwig, Jones, and Kilen (1991). Standard check genotypes may also be identified empirically for other species and micronutrients.

Second, the plant species and strains must be capable of providing both parent phenotypes (male fertility and male sterility/female fertility) inducible by a particular micronutrient deficiency. Some plant species are more susceptible to fertility effects due to a deficiency for a micronutrient, such as wheat, and these are preferred. Within such a species, individual homozygous lines may be selected which consistently demonstrate a particular fertility effect under particular conditions of micronutrient deficiency or sufficiency. Some lines are male parents in the fertility-selective growth medium, and others are female parents. The selection of particular species and lines satisfying these requirements can be accomplished in the field or otherwise using methods known to plant breeders.

Third, the micronutrient must be chosen so that it has the desirable fertility-selective effect without critically damaging plant viability or otherwise disrupting female fertility. Boron deficiency has a fertility-selective effect in wheat but allows for viable female fertile plants. Copper deficiency has excessively disruptive effects in most known wheat lines. Other micronutrient-plant combinations can be selected according to the invention to accomplish the objectives of providing differential fertility in a micronutrient deficient environment.

Fourth, the concentration of micronutrient available to the plant should be adjusted to a level low enough to induce male sterility in mother plants, but sufficient to maintain viability and female fertility. The latter requirement may be satisfied by supplemental application of the micronutrient to the female parent, sufficient to promote grain set, but not so high as to cause toxic effects, or to alter the male sterility status.

Fifth, the timing of the deficiency must be such that the desired phenotypes are achieved. A deficiency may be required at one point in the life cycle to cause male sterility in the female parent, while a sufficiency is required later to promote female fertility. For example, eliminating a boron deficiency in a female plant by foliar boron application prior to pollination promotes fertility.

According to the invention, the effects of micronutrient deficiency are used to permit economical cross-pollination of rice, wheat, barley, and related crops. A method for producing hybrid plant seeds according to the invention comprises (a) identifying fertility-selective media by use of standard check genotypes, (b) selecting two parent plants of the same species having different genotypes, the mother plant having a phenotype of female fertility and reduced male fertility when grown in a fertility-selective growth medium deficient for a micronutrient, and the father plant having a phenotype of male fertility, (c) raising the plants to sexual maturity, (d) transferring pollen from the father plant to the mother plant to cause genetic transfer, (e) raising the mother plant to produce hybrid seeds having genetic material from both parents, (f) harvesting the hybrid seeds.

The present invention provides an agronomic method of controlling sexual reproduction in a plant, comprising:
 (a) growing the plant in a micronutrient-deficient growth medium; and
 (b) selecting a male sterile plant.

The term "sexual reproduction" is used in reference to a method of producing new generations in which a plant arises from a zygote which is formed as a result of the fusion between two gametes or nuclei. In general, one gamete is produced by a male gonad and one gamete by a female gonad. The term "sexual reproduction" is to be taken in its broadest context to include the process of gametogenesis, or gamete formation, with particular reference to "male gametogenesis" which in the plant kingdom is the process whereby pollen is formed. Sexual reproduction also includes the process of pollination, whereby mature pollen is transferred from the anthers to the stigma of an angiosperm, or from the male cone to the female cone of a gymnosperm, to cause gametic fusion and produce a zygote having the genetic material of both the male and female gametes.

If the pollen transfer occurs between two different flowers on genetically different plants, or between genetically distinct flowers, it is termed "cross-pollination". Cross-pollination results in genetic recombination. Cross-pollination can be achieved manually, or blocked for example by bagging flowers of a plant. Pollination preferably is allowed to occur by natural forces including wind and insect transport.

If the transfer occurs in the same flower, or between different flowers of the same plant it is termed "selfing" or "self-pollination". Such plants are self-compatible, and produce progeny primarily by inbreeding, so that they breed true from generation to generation. The relative frequencies of self-pollination and cross-pollination vary considerably between plant species. Some plants, for example, tobacco, are exclusively out-breeding, having developed a complex self-incompatibility system to prevent self-pollination, and thereby increase genetic variation. Other plants such as wheat, rice, and barley are predominantly in-breeding and utilize self-pollination mechanisms almost exclusively. Such plants can be subjected to cross-pollination according to the invention. In angiosperms, a number of factors, for example flower morphology and the relative maturation time of anthers and stigmas, determine the relative frequencies of self-pollination and cross-pollination within a given plant species.

The term "controlling sexual reproduction" refers to any alterations to the mechanisms of sexual reproduction which normally operate in vivo, for a particular plant species. For a plant species in which sexual reproduction involves a self-pollination mechanism, the male sexual organ may be rendered sterile prior to pollen maturation, such that the female sexual organ, when mature, is receptive to pollen from a different donor plant, usually of the same species, and fusion of the gametes can occur. The pollen donor plant has a different genotype than the recipient plant, or male sterile plant, so as to produce a hybrid seed.

Fertility-selective growth media according to the invention are now discussed. Micronutrients include boron, copper, iron, manganese, molybdenum, zinc, and cobalt. These are distinguished from the macronutrients such as calcium, phosphorous, nitrogen, potassium, magnesium, and sulfur.

A micronutrient-deficient fertility-selective growth medium is one which restricts the uptake of the micronutrient by a mother plant to a level which is insufficient for production of mature pollen, but provides fertile female flower parts. This in turn precludes sexual reproduction by means of self-pollination, but allows cross-pollination to occur. Preferably, the same growth medium supports production of mature pollen in a father plant of a different genotype.

The deficiency may be a low stoichiometric level of the micronutrient or its biological unavailability. An important feature is that the micronutrient is not available to the mother plant in sufficient levels to produce mature pollen. The medium typically includes the solid and liquid phases of the rooting matrix in which the plant grows. However, the term medium as referred to here also includes the entire environment supplying micronutrients to the plant, including that of the plant's upper portions. For example, if a micronutrient is supplied to the plant's leaves and stalks by means of transfer from the air or liquid applications, so that the micronutrient is present in sufficient quantity to allow pollen to mature, then this would not be a micronutrient-deficient growth medium.

The growth medium may be soil, sand, vermiculite, or any other appropriate naturally occurring or man-made growth medium for the plant to be hybridized. Preferably, the micronutrient-deficient growth medium is soil in which the plant is growing, in a field or in a container. The minimum level of a micronutrient required for a plant to reproduce sexually varies considerably, depending on the micronutrient and species, and there is some variation between varieties or cultivars of the same species. By use of standard check genotypes, the minimum level of a particular micronutrient required for any plant to reproduce sexually and the maximum level at which the fertility-selective effect is evident may be determined. This range may vary with the type of growth medium (clay content, type of clay, pH), external environment (water, climate and other factors). In light soils the critical level for boron may be about 0.1 mg B/kg soil. In heavier soils the level is higher. In calcareous soils, the level may be as high as 0.2–1 mg B/kg.

Preferably, the father and mother plants may be raised in the same medium throughout their growth cycle. This is the most economical approach. Alternatively, the father is separately raised in a different location and/or growth medium. After fertilization, the mother plant may be removed to a different growth medium, or treated with a nutrient solution containing the micronutrient for which the growth medium is deficient.

The availability of micronutrient to a plant may be controlled in various ways. Some soils are appropriately deficient due to overcropping or natural causes. Soil and other growth media can have the availability of the micronutrient altered by the application of a sequestering agent or other appropriate soil amendments to the soil.

Sequestration is the suppression of the bioavailability of a micronutrient, without removing it from the growth medium. In the present context, the bioavailability of a micronutrient to be suppressed is its ability to be utilized by a particular target plant in such a way as to enable the plant to develop the desirable phenotype according to the invention (female fertility/male sterility or male fertility).

In the present context, sequestration is taken to include a process whereby the pH of a soil is increased, resulting in a change in the solubility of a micronutrient such that it is less available for uptake and utilization by a plant. Preferably, this action results in a shift in soil pH to pH values ranging between 7.5 and 8.5. It will be readily understood by those skilled in the art, that the shift in soil pH which is obtained following application of a sequestering agent may vary, depending upon the soil type and the micronutrient to be sequestered.

To be practical, the sequestering and/or neutralizing agent must not cause any undesirable change to the plant or the soil that would render the system unsuitable for its intended purpose. Sequestration reduces the concentration of available micronutrient to a very low value, by converting the micronutrient to a form that does not possess the properties to be absorbed by plants.

In a preferred embodiment of the present invention, the micronutrient is sequestered or otherwise made unavailable to the plant, by the application of chemical compounds containing calcium oxide and/or calcium carbonate, and/or calcium hydroxide, and/or magnesium salts as an active constituent, present for example in various forms of lime, dolomite, or gypsum. Preferably, the sequestering agent of the present invention contains a sufficiently low level of micronutrients to enable it to be capable of sequestering said micronutrient, or otherwise preventing utilization of said micronutrient by the plant.

Alternatively, the pH could be lowered by an amendment to below 7.0, e.g. 6.5, 5.5 or less, to reduce availability of another micronutrient which is less available in more acid medium.

Without intending to be bound by any theory or mode of action, the application of lime or dolomite to the soil may exert their effect on the plant primarily by increasing the pH of the soil. As exemplified in the present application, liming of the soil resulted in a substantial shift in soil pH from 6.4–6.8 to 6.8–7.0 at Chiang Mai, with concomitant male sterility detected in several lines of bread wheat.

Rates of applications of lime for the present purpose vary greatly depending on many factors, the low micronutrient or micronutrient content of the soil, for example, the critical low micronutrient or micronutrient concentration required by the target plant to achieve sexual reproduction, the species of target plant, and soil type including soil pH, amongst others. Application rates are determined empirically by routine experimentation.

The present invention extends to other methods by which a micronutrient is made less available to plant by restricting, or otherwise reducing the ability of the plant to extract the micronutrient from the growth medium. Such methods include, but are not limited to, reducing water availability, or waterlogging the growth medium.

Another aspect of the invention provides a method for the production of a hybrid comprising the steps of:
  (i) producing a male sterile female fertile parent plant by growing the plant in a micronutrient-deficient environment;
  (ii) spraying the male sterile parent plant with a micronutrient solution containing micronutrient in which said plant is deficient for the purpose of achieving sexual reproduction and wherein the micronutrient is one or more metals selected from the list comprising boron, iron, manganese, copper, zinc, or molybdenum;
  (iii) cross-pollinating the male sterile plant with pollen from a pollen donor plant to achieve fertilization;

Pollen tubes of fertile donor pollen may not extend vigorously when used to fertilize the stigmas of a male sterile plant which is produced by growth in a micronutrient-deficient environment. While not being bound by any theory or mode of action, the step of spraying stigmas of the female parent with a micronutrient spray prior to fertilization may stimulate pollen germination and/or growth of the pollen tube. It will be understood by those skilled in the art how to vary the conditions used to pre-treat stigmas with said micronutrient spray, to increase the frequency of hybrid seed set by cross-pollination of different species, or under different growing conditions.

Preferably, the micronutrient for which the fertility-selective growth medium is deficient is boron. Boron levels may be determined as hot water soluble boron in soil, boron concentration in nutrient solution fed to plants maintained in soil, vermiculite, or other boron-free media, or boron concentration in solutions for foliar application. Boron levels in plant tissue can be determined by the azomethine-H method, Lohse, G., "Microanalytical azomethine-H method for boron determination in plant tissue," *Commun. Soil Sci. Plant Anal.* 13:127–134 (1982). Other methods of measuring micronutrients are known to those in the art.

In soil, the bioavailable concentration range of deficient micronutrient may be between about 0.0001 and about 2 mg/kg soil, preferably between about 0.01 and about 1 mg/kg soil. For boron the concentration range may be between 0.05 and about 2 mg hot water soluble boron/kg soil, preferably between about 0.05 and about 1 mg hot water soluble boron/kg soil, and most preferably between about 0.09 and 0.5 mg hot water soluble boron/kg soil. For copper the concentration range may be between about 0.001 and about 2 mg bioavailable Cu/kg soil, preferably between about 0.01 and about 2 mg bioavailable Cu/kg soil, and most preferably between 0.01 and about 1 mg bioavailable Cu/kg soil. For manganese the concentration range may be between about 0.001 and about 2 mg bioavailable Mn/kg soil, preferably between about 0.01 and about 2 mg bioavailable Mn/kg soil, and most preferably between about 0.01 and about 1 mg bioavailable Mn/kg soil. For zinc the concentration range may be between about 0.001 and about 2 mg bioavailable Zn/kg soil, preferably between about 0.01 and about 2 mg bioavailable Zn/kg soil, and most preferably between about 0.01 and about 1 mg bioavailable Zn/kg soil. For molybdenum the concentration range may be between about 0.001 and about 0.1 mg bioavailable Mo/kg soil, preferably between about 0.001 and about 0.1 mg/kg soil, and most preferably between about 0.001 and 0.05 mg bioavailable Mo/kg soil.

In manmade media, the concentration of all micronutrients is generally almost nil, usually below about 0.001 micromolar to 0.01 micromolar. The concentration of the deficient micronutrient in nutrient solution may be between about 0.001 micromolar and about 1 micromolar, and preferably between about 0.001 and about 0.5 micromolar.

For boron the concentration range may be between about 0.001 and about 2 micromolar, preferably between about 0.005 and about 1 micromolar, and most preferably between about 0.01 and about 1 micromolar. For copper the concentration range may be between about 0.001 and about 2 micromolar, preferably between about 0.005 and about 1 micromolar, and most preferably between 0.01 and about 1 micromolar. For manganese the concentration range may be between 0.001 and about 2 micromolar, preferably between about 0.005 and about 1 micromolar, and most preferably between 0.01 and about 1 micromolar. For zinc the concentration range may be between about 0.001 and about 2 micromolar, preferably between about 0.005 and about 1 micromolar, and most preferably between 0.01 and about 1 micromolar. For molybdenum the concentration range may be between about 0.001 and about 0.5 micromolar, preferably between about 0.0005 and about 0.2 micromolar, and most preferably between 0.001 and about 0.1 micromolar.

The concentration range of micronutrient that is applied directly to the plant to assist in the fertilization process or to supply the female part of the flower or other non-reproductive part of the plant may be between about 0.01% and about 1%, w/v, applied to give the rate of about 0.01 kg/ha and about 5 kg/ha, preferably between about 0.05% and about 0.5%, w/v, to give the rate of about 0.1 kg/ha and about 1 kg/ha. For boron the concentration range may be between about 0.01% and about 1%, w/v, giving between about 10 g/ha and about 500 g/ha, preferably between about 0.02% and about 1%, w/v, giving between about 20 g/ha and 200 g/ha. For copper the concentration range may be between about 0.01% and about 1%, w/v, giving between about 10 g/ha and about 500 g/ha, preferably between about 0.02% and about 1%, w/v, giving between about 20 g/ha and about 500 g/ha. For zinc the concentration range may be between about 0.01% and about 1%, w/v, giving between about 10 g/ha and about 500 g/ha, preferably between about 0.02% and about 1%, w/v, giving between about 20 g/ha and about 200 g/ha. For manganese the concentration range may be between about 0.01% and about 5%, w/v, giving between about 10 g/ha and about 500 g/ha, preferably between about 0.05% and about 1%, w/v, giving between about 20 g/ha and about 200 g/ha. For molybdenum the concentration range may be between about 0.01% and about 0.1%, w/v, giving between about 10 g/ha and about 100 g/ha, preferably between about 0.005% and about 0.05%, w/v, giving between about 20 g/ha and about 80 g/ha.

Deficiency-sensitive plants according to the invention are now discussed. In general, the present invention provides for the production of a male sterile plant belonging to certain monocotyledonous or dicotyledonous plant species in the same way of wheat responding to boron. In a preferred embodiment of the present invention, the plant is a monocotyledonous plant species, selected from, but not limited to the list comprising: wheat, barley, rice, rye, triticale, maize, sorghum, or millet. In a particularly preferred embodiment of the present invention, the plant is a self-fertilizing small grain cereal crop plant, for example wheat, rice, barley, or oats. The present invention contemplates additional species. The mother plants can be varieties of wheat, rice, barley, or any other flowering plant having reduced male fertility in a micronutrient-deficient growth medium.

The method of the invention applies to any plant species which responds to a micronutrient deficiency and/or management of the micronutrient in the same way as wheat responding to boron deficiency. This involves (i) greater sensitivity to the deficiency in the male parts of the flowers than the female parts; and (ii) greater sensitivity in the reproductive male parts than the non-reproductive parts; or, if not (i) and (ii), at least (iii) micronutrient application can be managed in such a way to restore female fertility and supply other non-reproductive requirements (e.g. spraying a micronutrient solution). Factor (i) is important because otherwise there is no female fertility. Factor (ii) is important because otherwise the reproductive parts may fall off entirely, as with sunflowers, some fruits and some beans, for which one of the first signs of boron deficiency is shedding of flower buds.

Figure 1E:
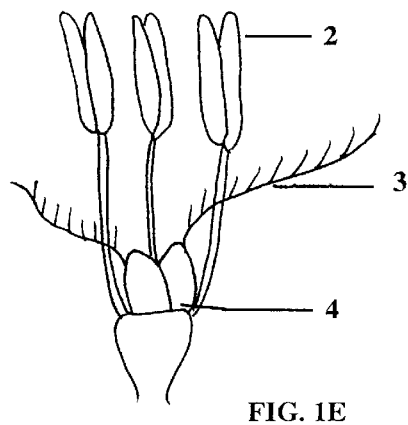
FIGS. 1E–1H schematically show male parts (sterile anthers 5 on filaments), female parts (stigmas), and lodicules, just before anthesis, for different degrees of male fertility/sterility.
Figures 1F, 1G, 1H:
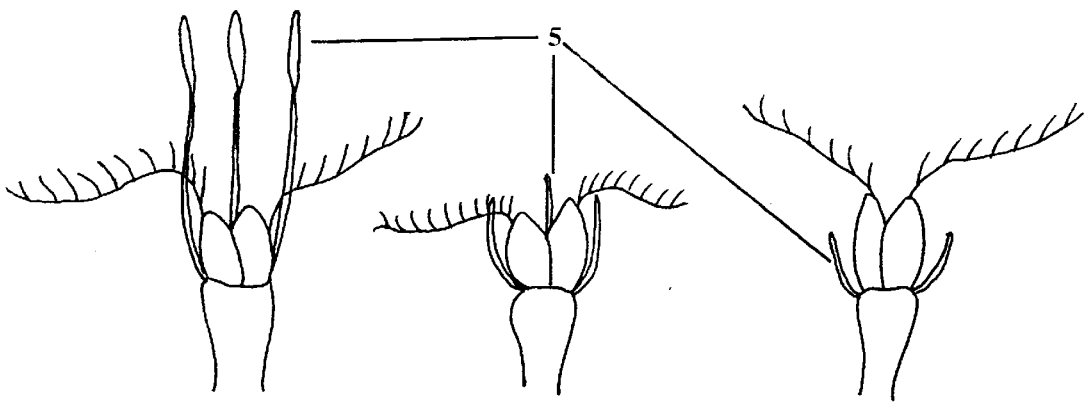
Figure 2A:
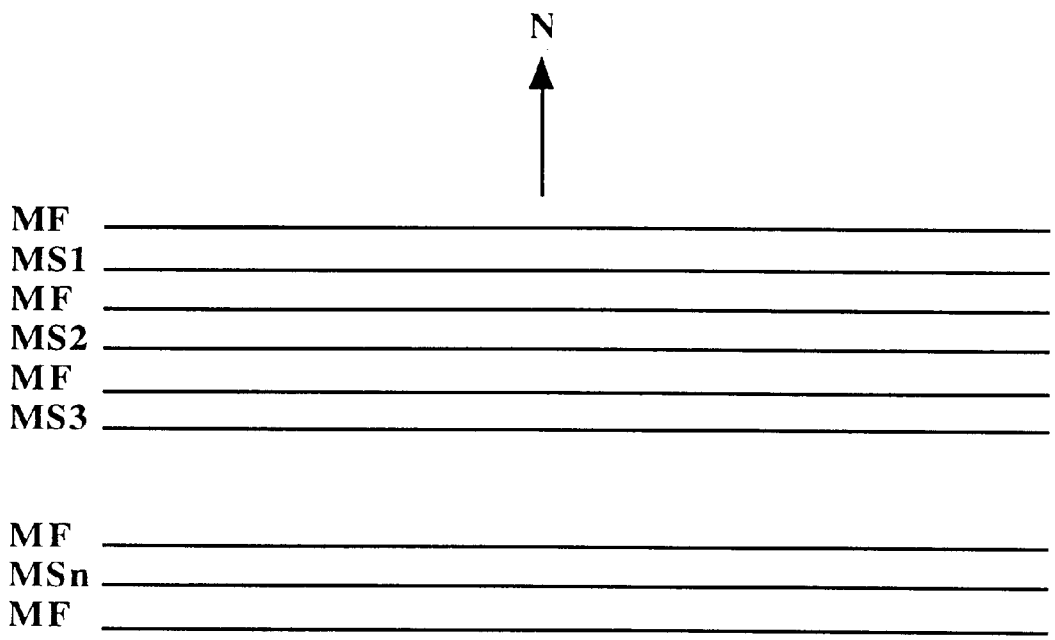
FIG. 2A shows the proximity between male sterile/female fertile (MS) and male fertile (MF) genotypes of wheat arranged in a field with fertility-selective soil. Each MS genotype was sown in a 3 m row, with a row of MF plants on either side, 25 cm apart.
Figure 2B:
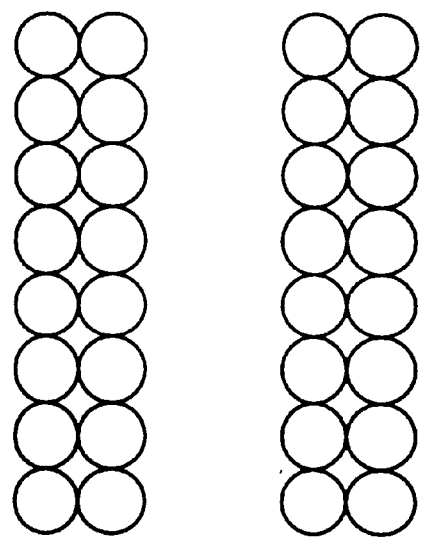
In FIG. 2B, earthenware pots were used, 30 cm in diameter and 30 cm deep. Double rows of pots were placed 50 cm apart. Each pot contained about 5–10 plants of a MS or a MF genotype. Each pot was watered individually by hand or by drip irrigation with nutrient solution.

Another aspect of the present invention extends to a male sterile plant produced by growing the plant in a micronutrient-deficient environment. The male sterile plant of the present invention is useful for the production of hybrid seed. Male sterile plants produced according to the present invention exhibit one or more of the following morphological characteristics: arrested development of pollen at any stage; degraded anther structures prior to pollen maturation;

arrested development of anther structures prior to pollen maturation; no visible dehiscence of anthers; empty locules; failure of pollen to germinate and grow a pollen tube when contacted with the female sexual organ; reduced levels of pollen production; gaping florets at anthesis; and reduced fecundity when the plant is allowed to self-pollinate. Some of these effects are shown in FIGS. 1F to 1H.

For boron, suitable male parent wheat plants include Fang 60, Sonora 64, CMU-F2, CMU-F3, CMU-F4, CMU-F5, CMU-F6, CMU-F7, CMU-F8, CMU-F9, CMU-F10, and CMU-F11. For these lines anthers and pollen are "normal", i.e. anthers are regular in shape, size, color and number of pollen grains, pollen is regular in size and shape and essentially all stain black in potassium iodide/iodine solution), and grain set index (GSI) is about 80–100%.

Preferred male parents having male fertility in limed soil with less than about 0.14 mg hot water soluble boron per kilogram (mg HWSB/kg) include: Fang 60, Sonora 64, CMU-F2, CMU-F3, CMU-F5, CMU-F6, CMU-F7, and CMU-F8. In soil with less than about 0.10 mg hot water soluble boron per kilogram (HWSB/kg) the following male parents are preferred: Fang 60, CMU-F4, CMU-F7, and CMU-F8. In sand culture, with less than about 0.2 micromolar boron, the following male parents are preferred: Fang 60, CMU-F4, CMU-F9, CMU-F10, and CMU-F11. Also, in limed soil, F1's with Fang 60 as the male parent that can be used again as male parents, as they are male fertile, include Veery X Fang 60, Sunelg X Fang 60, 84Z;1156 X Fang 60, K11A-3 X Fang 60, $U^2$K212B-4 X Fang 60, SUN211A X Fang 60, 82Y;1185 X Fang 60, RAC730 X Fang 60, and SW41 X Fang 60.

Suitable female parent wheat plants, which are male sterile in fertility-selective growth media, include: CMU-M1, CMU-M2, CMU-M21, RAC730, 84Z;1156, Kite, $U^2$K212B-4, Tatiara, Lin Calel, 82Y;1185, (YR10WARx)1/1, K11A-3, Sunelg, Bonza, Gamenya, Warrigal, QT5648, Aroona, K113-A, Sundor, SUN276A, K1182, EL240, Bd9, Veery, Eradu, Kenya Farmer, ED089, Schombergk, BT Schombergk, Spear, Machete, Wilgoyne, Kite, CMU-M12, CMU-M23, CMU-M24. For these lines, anthers and pollen are "malformed", i.e. anthers are shrivelled, small to absent and pollen grains are few, small and misshapened and do not stain in potassium iodide/iodine solution, and GSI is about 0–5% (i.e. <2 grains/ear). Also suitable as female parents, although they have some male fertility in the fertility-selective media, are CMU-M9, CMU-M27, BD231, ED135, Egret, Halberd, QT4546, QT4639, RAC710, SUN211A, SUN250c, Suneca, SW41, Tabuk, and WW1248.

Preferred female lines in limed soil with less than about 0.14 mg HWSB/kg include: $U^2$K212B-4, Sunelg, Bonza, Gamenya, Warrigal, QT5648, Aroona, K113-A, RAC730, Tatiara, Sundor, (YR10WARx)1/1, SUN276A, K1182, EL240, Bd9, Veery, Eradu, Kenya Farmer, ED089, Schombergk, BT Schombergk, Spear, Machete, Wilgoyne, Kite, CMU-M12, MU-M23, CMU-M24. Preferred female parents having male fertility in soil with less than about 0.10 mg HWSB/kg include: CMU-M1, CMU-M2, CMU-M21, RAC730, 84Z;1156, Kite, $U^2$K212B-4, Tatiara, Lin Calel, 82Y;1185, (YR10WARx)1/1, K11A-3, and Sunelg. In sand culture, with no boron added, and boron in nutrient solution <0.2 micromolar, CMU-M9, CMU-M27, (YR10WARx)1/1, 82Y;1185, 84Z;1156, BD231, Bd9, Bonza, BT Schombergk, ED089, ED135, Egret, Eradu, EL240, Gamenya, Halberd, K1182, K11A-3, Kite, Machete, QT4546, QT4639, QT5648, RAC710, RAC730, Schombergk, Spear, SUN211A, SUN250c, SUN276A, Suneca, Sunelg, SW41, Tabuk, Tatiara, $U^2$K212B-4, Veery, Warrigal, Wilgoyne, and WW1248. Also, in limed soil, F1's, with Fang 60 as the male parent that can be used again as female parent, as they are male sterile, include Tatiara X Fang 60, (W1×MMC)/W1/10 X Fang 60, EL240 X Fang 60, Kenya Farmer X Fang 60, and Warrigal X Fang 60.

Preferably, when self-pollinated, a male sterile plant will achieve a seed set which is only about 20% of the seed set of a selfed isogenic plant grown under the same conditions but without micronutrient deficiency. More preferably, the selfed male sterile plant induced by micronutrient deficiency will set seed at only about 10 to about 20% of the level of a selfed isogenic plant grown under the same conditions but without micronutrient deficiency. Still more preferably, the selfed male sterile plant induced by micronutrient deficiency will set seed at only about 5 to about 10%, and even still more preferably at 0 to about 5%, of the seed set obtained when an isogenic plant grown under the same conditions, but without micronutrient deficiency, is selfed. Methods for the identification of male sterile plants are well-known to those skilled in the art.

The male sterile plant, when cross-pollinated, should have female fertility sufficient to achieve a grain set of greater than 30%, preferably over about 50%, more preferably over about 80%, and most preferably over about 90%.

In general, the level of grain set is determined by Grain Set Index (GSI) which measures the percentage of basal florets (2 per spikelet) of central spikelets (about 10 per ear) which are always likely to be competent, and filled when fertilized. In manually fertilized ears, the percentage of flowers with grains is automatically considered an estimation of grain set.

"Grain set" is a process reflected in the success of fertilization of an ovary by pollen. Grain set is normally measured by counting the number of flowers and the number of grains. The percentage (i.e. % flowers with grain) derived from this, however, is the ultimate result of different processes: (1) flower development, (2) grain set (i.e. male× female fertilization) and (3) grain filling. The Grain Set Index is an index that measures the number of grains only in those flowers that can always be expected to develop fully (i.e. (1) OK) and always get filled if they are fertilized (i.e. (3) OK). These are the flowers of the two basal florets of spikelets from the middle of the ear. Any variation encountered in GSI is likely to be because of success or failure in (2), i.e. "grain set". Normally, when making manual crosses one knows exactly how many flowers have been crossed, and one normally only crosses those flowers that have developed fully. Those flowers that are incompetent in an ear pinched or snipped out. Flowers that are crossed are normally the first two from the base of a spikelet, which are always filled when fertilized. The percentage of flowers with grain is the result of success or failure of the fertilization process, and the percentage of flowers with grains becomes "% grain set".

A preferred embodiment of the present invention contemplates a method for producing hybrids with desirable traits, wherein the hybrid is the progeny of a pollen donor plant, and a male sterile parent plant produced as hereinbefore described, and both parent plants are selected such that, when their respective gene pools are combined through the process of sexual reproduction, and heterosis comes into play, the progeny thus obtained exhibit one or more desirable traits when compared to either parent, for example: increased resistance to pathogens, increased stress tolerance, reduced maturation time, greater yield, better agronomic quality, uniformity of shape and size, and customized grain which is more suitable for downstream processing.

The present invention extends to a hybrid plant produced according to the methods as hereinbefore described. Preferably, the hybrid achieves 10% increased yield compared to the better parent. More preferably, the hybrid achieves 10% to 25% increased yield, compared to the better parent. Still more preferably, the increased yield in the hybrid is 25% to 50%, even still more preferably 50% to 100% and, in a most preferred embodiment, 100% to 250%, compared to the better parent.

A preferred embodiment of the invention may be referred to as a screening and crossing scheme for producing hybrids having three basic steps, and may be schematized as follows.
1. Identify appropriate level of micronutrient for fertility-selective media
2. Screen in low micronutrient fertility-selective media to obtain inbred lines
3. Hybridization of the inbred lines in fertility-selective media

| MS | X | MF | --> | F1 |
|---|---|---|---|---|
| male sterile/ female fertile parent | | male fertile parent | | hybrid |

Step 1: Identifying Appropriate Fertility-Selective Media

The purpose of STEP 1 of invention is to identify media that will give appropriate degrees of sterility/fertility in the male and female parents. The media are chosen on the basis of sterility/fertility of genotypes with known responses to the micronutrient deficiency.

At a sufficiency standard check genotypes should have Grain Set Index (GSI) 85–100%. A fertility-selective medium is chosen as one that gives GSI 0–20% in sensitive genotypes and 85–100% in tolerant genotypes, i.e. (GSI tolerant genotype) minus (GSI sensitive genotype) approaching 100%. Alternatively, the difference may be at any predetermined level, e.g. (GSI tolerant genotype)–(GSI sensitive genotype) at $\geq 20\%$, or at $\geq 30\%$.

This step may be used for any micronutrient deficiency. For boron deficiency in wheat, any genotypes with known responses can be used as standard checks. Those that have been well tested include Fang 60 and Sonora 64 for male fertility, and SW41 and B1022 for male sterility. For limed soils, genotypes that have repeatedly shown to be about 100% male sterile such as Tatiara and Gamenya may also be used as standard checks. The low boron rooting medium may be (a) a soil that naturally contains little boron; (b) a soil that has had its available boron content depleted by cropping practices such as repeated cropping (see Example 2), or application of soil fertilizers and amendments such as liming (see example 3); or a man-made medium (see Example 4).

Step 2: Production of Male Sterile/Female Fertile Mothers and Male Fertile Fathers The purpose of STEP 2 of the invention is to select plants of the same species which differ in their levels of male sterility when grown under a particularly specified condition, i.e. some are male sterile but female fertile and some are male fertile. These male sterility/fertility traits must also breed true to type, i.e. be genetically based and therefore fully heritable from one generation to the next. The degree of male sterility/fertility may be at any chosen level. If the plant is less than 100% male sterile, a proportion of the seed produced from the cross will not be hybrid seed.

A wide range of genotypes of plants of the same species are grown in rooting medium that is sufficiently low in a micronutrient to create a phenotype of male sterility in some individuals and not in others. The low micronutrient rooting medium may be (a) a soil that naturally contains little of the micronutrient; (b) a soil that has had its available content of the micronutrient depleted by cropping practices such as repeated cropping (see Example 2 for boron), or application of soil fertilizers and amendments such as liming (see Example 3 for boron); or (c) a man-made medium (see Example 4). The level of male sterility/fertility in each genotype is assessed by examining the anthers and pollen, and by evaluating grain set when each genotype is self-fertilized. Grain set from self-fertilization may be evaluated by bagging the flowers to prevent cross-fertilization from other plants.

Plants are selected based on their ability to breed true to type with any chosen level of male sterility/fertility in any particularly specified level of micronutrient deficiency. The genetics of male sterility/fertility may be further manipulated by transferring relevant genes. Conventional breeding methods of cross-fertilization may be used, or molecular genetics means of implanting new genes in a particular specimen, to combine differential fertility phenotypes with other biologically and agronomically desirable traits. The resultant genotypes may be again used as fathers (if they are male fertile) or mothers (if they are male sterile) in hybrid seed production.

Step 3: Combining the Genes to Produce Hybrids

The purpose of STEP 3 of the invention is to combine genes from the two parents by growing together, under a particularly specified condition, plants of a male sterile type and a male fertile type so that the pollen (male gametes) from the male fertile plants is transferred to fertilize the male sterile but female fertile plants, thus to produce seeds that are hybrids or heterozygous. Pollen transfer may occur, naturally, with the aid of insects, wind or air movement, or assisted in various ways manually, such as by shading the male fertile plants.

Plants from a pair of genotypes selected as in step 2 are grown together in a particularly defined level of micronutrient deficiency that makes plants of one type male sterile/female fertile (the mother) and one type male fertile (the father). They are preferably managed in such a way that flowering in the two plant types is synchronized and cross-fertilization occurs naturally, aided by winds or by hand (Examples 5 and 8). This is done in the same rooting media as in step 2, i.e. soil that is naturally low in a micronutrient or has become micronutrient-depleted in the course of repeated cropping (as in Example 2); soil that has been fertilized or amended (e.g. limed as in Example 3) or artificial media for growing plants (as in Example 4). The success of this gene combination can be enhanced by various common crop management practices, including spraying with a solution of the micronutrient, a method that is suitable for correcting micronutrient deficiency in growing plants (as in Example 6).

The invention provides a novel, less laborious, and economical method for combining plant genes. The invention can therefore be used for producing seeds that are heterozygous (hybrids) after one cross (single cross, F1 progeny) or two or more crosses (Example 7), which have higher yields and other superior qualities.

Uses of the F1 hybrids include the following: F1 hybrid seed can be grown into crop plants to gain the benefits of heterosis. Alternatively, F1s can be selected, with or without further crosses to incorporate more desirable traits (including standard procedures such as backcrossing), through several generations, until homozygous again to produce a new inbred line that will breed true. Finally, F1s may be screened in fertility-selective media to determine whether they can be used for further hybridization. Thus, the F1 plant may be (A) male fertile (potential male parent), F1-MF; or (B) male sterile (potential female parent), F1-MS. These phenotypes allow for the following types of further crosses using F1s.

also be used to produce composite varieties—mixtures of several phenotypically similar lines, which are genotypically different, for purposes of enhanced disease resistance. N. E. Borlaug, "New approach to the breeding of wheat varieties resistant to Puccinia graminis tritici," *Phytopathology* 43:467, abstr. (1953); N. E. Borlaug, "The use of multilineal or composite varieties to control airborne epidemic diseases

| a. MS | X F1-MF | --> | hybrid (three-way) |
|---|---|---|---|
| inbred line as female parent male sterile | F1 as male parent, male fertile | | |
| b. F1-MS | X MF | --> | hybrid (three-way) |
| F1 as female parent, male sterile | | inbred line as male parent, male fertile | |
| c. F1-MS | X F1-MF | --> | hybrid (double cross) |
| F1 as female parent, male sterile | | F1 as male parent, male fertile | |

The hybridization process can also be used to combine genes for any other desirable biological and agronomic characteristics or traits including resistance to diseases. Thus the invention can be used by seed companies to produce "superior" seeds which result from various combinations of genes.

The superior seeds according to the invention may be used directly to grow a crop, while their genetics are still heterozygous, as in single crosses or F1 hybrids, or three-way crosses between an F1 and an inbred line, or double-crosses (four way crosses) between two F1s, and so on.

After the genes are combined, the heterozygous plants may be grown and selected for several generations until they are homozygous and the superior combination of genes is stabilized, i.e. will no longer segregate and breed true. Thus, the new "improved" variety can be grown and perpetuated by farmers themselves, i.e. with no further cost of seed for each new sowing.

Thus, the ultimate purpose of the invention is to make it simpler, more economical and less laborious to combine genes of plants of the same species, in order that "new" and superior plants can be selected from these various gene combinations.

In a most preferred embodiment of the invention, the genetic manipulation of plants is directed toward identification and selection or transfer of genes (by conventional methods of cross-pollination, or molecular genetic manipulation, or other methods described herein), so that when grown under a particularly specified condition, some types are 100% male sterile and 100% female fertile and some types are 100% male fertile. The genes of such parents may be combined naturally or with some simple manual aids.

In other preferred embodiments, plants that are less than 100% male sterile in a particular specified level of boron deficiency may also be selected as mothers. The hybrids produced may be less than 100% pure, but this genetic diversity may have other desirable characteristics. For example, crosses made with female parents that are less than 100% male sterile may be useful in creating "multilines" N. F. Jensen, "Intervarietal diversification in oat breeding," *Agronomy Journal*, 44:30–34 (1952). This approach may of self-pollinated crop plants," *First Int. Wheat Genet. Symp. Proc.*, University of Manitoba, Winnipeg (1958), pp. 12–27.

Plants that are less than 100% male fertile in a particular specified level of micronutrient deficiency may also be selected as fathers. The degree of cross-fertilization may be lower than with highly male fertile plants, but the plant with low fertility may have other desirable traits for producing a hybrid that justify such inefficiency of hybrid seed production. The level of male fertility may be increased by targeted application of the micronutrient to a particular part or organ of the growing plant.

Boron Deficiency Determination

The level of boron in the male reproductive organs can be determined by any method of chemical analysis (e.g. Loshe, G., "Micro analytical Azomethine-H method for born determination in plant tissue," *Commun. Soil Sci. Plant Anal.* 1:13–19, 1982; Zarcinas B. A., B. Cartwright and L. R. Spouncer, "Nitric acid digestion and multi-element analysis of plant material by inductively coupled plasma spectrometry," *Commun. Soil Sci. Plant Anal.* 18:131–146, 1987), and expressed as mg B $kg^{-1}$. Plant samples are preferably dried in ventilated oven at 80 degrees C. for 48 hours. Larger samples (whole plants, ears, leaves) are ground, anthers are not. Subsamples (about 100–300 mg) are dry ashed (heated at 500 degrees C. for 8 hours), boron content of the ash is determined by developing colour with Azomethine-H (Merck) reagent and the intensity of the colour, which indicates concentration of B, is measured in a spectrometer. In the other method by Zarcinas et al, instead of dry ashing, dried plant samples are digested in concentrated acid and the boron content measured with an Inductively Coupled Plasma Spectrophotometer.

In wheat and other plants with similar inflorescence, the level of reproductive fertility can be determined as Grain Set Index, which is the percentage of 20 basal florets on the central spikelets with grain (Rerkasem and Loneragan, 1994). Published accounts have established that male sterility is primarily responsible for the reduction of Grain Set Index by boron deficiency (Cheng, C. and Rerkasem B., "Effects of boron on pollen viability in wheat," *Plant Soil* 155/156: 313–315, 1993.

According to the invention, the control of boron content of the male reproductive organs may be used to control the level of male sterility/fertility in wheat, rice, barley, rye, triticale, corn, sorghum, cotton, soybean, canola, broadbean, peas, and other suitable crops. The male reproductive organs comprise the anthers, pollen grains and other related tissues. A method for controlling the level of male sterility/fertility in plants comprises three steps, (a) determining the relationship between the boron content of the male reproductive organs and the level of male sterility/fertility, (b) determining the range of capacity to transport boron into the male reproductive organs in plants possessing different genotypes, (c) producing plants with the chosen level of male sterility/fertility according to the predetermined level of boron content in the male reproductive organs.

The method of this invention allows precise control of male fertility/sterility in wheat and other plants by controlling the boron content in their male reproductive organs. Boron content in the male reproductive organs may be controlled by choosing wheat plants possessing genotypes with desired capacity to transport boron into their male reproductive organs. This may be achieved according to the predetermined relationship between boron contents of the male reproductive organs by chemical analysis and degrees of male sterility. Preferably the plants are wheat, rice, barley, maize, triticale, and others.

In a preferred embodiment, the control of boron content of the male reproductive organs is used to control the level of male sterility/fertility in wheat. Preferably, the boron concentration in the wheat anthers at $\geq 11$ mg B kg$^{-1}$ dry weight indicates complete male fertility, which gives a Grain Set Index $\geq 85\%$ when self-fertilised. Preferably, boron concentration in the wheat anthers at $<11$ mg B kg$^{-1}$ indicates sterility, with increasing degree of sterility, and therefore lower Grain Set Index when self-fertilised, at lower boron concentration. A boron concentration in the wheat anthers at about 8 mg B kg$^{-1}$ dry weight indicates male sterility at about 50%, which gives a Grain Set Index of about 50% when self-fertilised. The boron concentration in the wheat anthers at $<6$ mg B kg$^{-1}$ dry weight indicates almost complete male sterility, which gives a Grain Set Index about 0%. Thus, preferably plants capable of achieving boron content $\geq 11$ mg/kg are selected as male parents (fathers) while plants at $<6$ mg B kg$^{-1}$ are selected as female parents (mothers).

In a particularly preferred embodiment of this invention, examples of wheat genotypes with capacity for different levels of boron content in their anthers are given as follows, though not restricted only to these:

| Anther boron capacity | Example genotypes |
| --- | --- |
| High | Fang 60 |
| Low | SW 41, Gamenya, Tatiara, Kite, Machete, Spear, Bonza, Eradu, Warrigal, Wilgoyne |

Plants possessing the genotypes that enable them to transport high levels of boron into their reproductive organs such as Fang 60 would be male fertile so can be used as male parents in hybridisation procedures. The genetic traits for ability to transport high levels of boron into the male reproductive organs can also be transferred to other plants with other desired characteristics as male parents. Conventional breeding or recombinant DNA techniques can be employed to obtain the advantages of the invention.

Plants possessing the genotypes that enable them to transport low levels of boron into their reproductive organs such as SW 41, Gamenya, Tatiara, Kite, Machete, Spear, Bonza, Eradu, Warrigal, Wilgoyne would be male sterile so can be used as female parents in hybridisation procedures. The genetic traits for ability to transport low levels of boron into the male reproductive organs can also be transferred to other plants with other desired characteristics as female parents.

In summary, this embodiment of the invention may encompass the following three steps.

A. Determining the Relationship between B Contents of Anthers and Male Sterility: The "fertility selective media" and standard B sensitive and tolerant genotypes are identified as in the general method above. Media that give a range of male sterility response (Grain Set Index when self fertilized from 0% to 100%) in the sensitive genotypes are used to grow plants with both B sensitive and tolerant genotypes. Anther B concentration is measured at a particular stage of growth, e.g. boot stage, ear emergence, but not after anthesis. Grain Set Index by self fertilization, which is a measure of male sterility, is assured by bagging ears e.g. (paper bags used by plant breeders), and determined (Rerkasem and Loneragan, 1994) when grain set has been completed at the earliest. The Grain Set Index data and anther B concentration are plotted together, GSI on Y-axis, anther B on X-axis. The precise relationship may be determined by various statistical procedures.

B. Determining the Range of Capacity to Transport B into the Anthers in Different Genotypes: According to the general method as above, genotypes with different sensitivity to B are identified. And in the "fertility selective media" they are grown at different levels of B in comparison with check genotypes with high anther B capacity (e.g. Fang 60) and low anther B capacity (e.g. SW41, Gamenya, Tatiara, Kite, Machete, Wilgoyn, Eradu, Warigal). As more than two classes have been identified among plant genotypes in their response to B, genotypes with different anther B capacity may be found, i.e. higher than Fang 60 or lower than SW41 et al. or in between.

C. Producing Plants with Chosen Level of Sterility According to the Predetermined B Content: Once the level of anther B that gives a particular desired level of male sterility has been determined in a particular genotype, the external environmental condition (in soil or artificial media for the roots, and other above ground climatics such as temperature, light, humidity, wind speed, etc. can be characterized, and used as the condition for producing a desired level of male fertility.

The following examples provide further details about preferred embodiments of the invention. They are not intended to limit the scope of the claimed invention.

EXAMPLE 1

Experimental Site and Details

The experiments described in the examples that follow were conducted in the growing season that lasts from October to March at Chiang Mai (18° 45' N latitude). Temperatures and rainfall data are shown for the last two growing seasons (Table 1).

TABLE 1

Climatic data during two growing seasons

| Year | Month | Mean Temperatures (° C.) Maximum | Minimum | Average | Rainfall (mm) |
|---|---|---|---|---|---|
| 1994 | October | 32.2 | 20.5 | 25.5 | 72.5 |
| | November | 31.2 | 17.6 | 23.4 | 55.6 |
| | December | 29.6 | 16.4 | 22.0 | 58.4 |
| 1995 | January | 31.0 | 14.7 | 21.7 | 0 |
| | February | 32.5 | 14.8 | 22.4 | 0 |
| | March | 36.7 | 20.1 | 27.2 | 0 |
| | October | 33.1 | 22.1 | 26.8 | 121.4 |
| | November | 30.1 | 19.6 | 24.1 | 26.3 |
| | December | 29.1 | 14.3 | 20.6 | 0 |
| 1996 | January | 30.6 | 12.2 | 20.1 | 0 |
| | February | 30.7 | 15.5 | 22.0 | 27.5 |
| | March | 35.8 | 19.0 | 26.2 | 19.1 |

Source: Weather Station, Multiple Cropping Centre, Chiang Mai University

The soil is a sandy loam with about 0.7% organic matter content. The original soil pH was about 6.5 and available boron (hot water extraction) averaged 0.14 mg B/kg soil. Wheat seed is generally sown at the rate of 5 g per 3 m row, with 0.25 m between rows. A genotype may be sown in single row or in an area (e.g. 1.5 m×3 m). Male sterile lines are often sown with potential pollen donors (e.g. Fang 60 or Sonora 64) in neighboring rows. Plants are also grown in a sand culture in pots, supplied with a nutrient solution with varied level of B supply.

Male fertility/sterility is assessed by:

(i) Examining anthers and pollen at ear emergence. A sample of two ears were taken from each line in each of the replicated blocks. Anthers from each six competent florets, from the middle of each ear, were examined under microscope, and pollen grains stained with potassium iodide/iodine solution. In selected cases every floret on the ear was examined.

(ii) Determining Grain Set Index (% GSI). This is the percentage of the 20 basal florets from central spikelets with grain set (observed in two basal florets of ten central spikelets in 5–10 ears). The plants were forced to self fertilize by bagging before anthesis. B. Rerkasem and J. F. Loneragan, "Boron deficiency in two wheat genotypes in a warm, subtropical region," Agron J. 86:887–890 (1994). This approach was taken in a Field Book Accompanying "Boron Probe Nursery", a collaborative experiment that was prepared at CMU, sent to collaborating scientists and published as Appendix 2, Boron deficiency nurseries, 1990/91, Pp. 126–128, in Mann, C. E. and Rerkasem, B. (eds.) Boron Deficiency in Wheat. CIMMYT Wheat Special Report No. 11. Mexico, D. F.: CIMMYT (1992).

The following examples 2, 3, 4 show how B deficiency (soil, man-made) was used as fertility-selective media in which wheat genotypes exhibited different degrees of male sterility and fertility.

Some of the wheat lines used in the examples are released lines that are publicly available; these have names or names and numbers. Other wheat lines used in the examples have letters and numbers; most of these are publicly available for example through CIMMYT, Thailand's Rice Research Institute, or analogous institutes in China, Nepal, Bangladesh, Australia, or elsewhere. Wheat lines identified with a CMU prefix are available from Chiang Mai University. Of the CMU lines, some are inbred lines from Thailand Observation Nurseries, some are repeats tested elsewhere also, and some are off-types.

EXAMPLE 2

Screening of Wheat Genotypes on a Soil with Boron Depleted by Repeated Cropping

The soil described in Example 1 had been growing two or three crops a year every year since 1970. By 1994 the hot water soluble boron had decreased to 0.09 mg B/kg. Hot water soluble boron (HWSB) is a useful measure of the amount of boron available for plant uptake. The greater the amount of HWSB, the more boron is available, and vice versa. On this soil 38 wheat genotypes had Grain Set Index that ranged from 0% to 100% when ears were bagged, i.e. self fertilized (Table 2). Table 2 shows grain set (Grain Set Index, %) in wheat genotypes in a soil with depleted boron (0.09 mg B/kg) due to repeated cropping. Eleven genotypes set no or just one grain per ear (GSI<3%), and four were fertile (GSI>80%). The remainder were in between these two extremes. When grown with applied B on near-by plot all genotypes were fully self fertile, i.e. GSI of bagged ears was >85% in all genotypes.

TABLE 2

Grain set in wheat genotypes in a soil with depleted B due to repeated cropping.

| Genotype[1] | Grain Set Index (%) Selfed (bagged) |
|---|---|
| Fang 60 | 100 |
| CMU-F4 | 97.5 |
| CMU-F7 | 82.5 |
| CMU-F8 | 87.5 |
| CMU-M1 | 0 |
| CMU-M2 | 1 |
| CMU-M21 | 2 |
| RAC730 | 0 |
| 84Z; 1156 | 0 |
| Kite | 0.5 |
| $U^2$K212B-4 | 0.5 |
| Tatiara | 1 |
| Lin Calel | 1 |
| 82Y; 1185 | 1 |
| (YR10WARx)1/1 | 2.5 |
| K11A-3 | 3.5 |
| Sunelg | 4.5 |
| Halberd | 12 |
| Gamenya | 13.3 |
| Eradu | 15 |
| SW41 | 19 |
| (WI*MMC)/W1/10 | 25 |
| EL240 | 25 |
| Spear | 27 |
| Kenya Farmer | 28 |
| QT4639 | 33 |
| WW1248 | 40 |
| ED135 | 41.5 |
| Warrigal | 42.5 |
| Benvenuto Inca | 48.3 |
| Egret | 34.5 |
| Sundor | 35 |
| ED089 | 36.3 |
| SUN211A | 36.7 |
| G61450 | 53 |
| RAC710 | 54.3 |
| Turkey 1473 | 68 |
| Aus4743 | 68.7 |

(1) "CMU" numbers designate un-named, un-released selections by Chiang Mai University. "F" designates potential father line and "M" potential mother line for producing hybrids.

EXAMPLE 3

Screening Wheat Genotypes in a Soil which has been Limed

Two experiments were conducted on the same soil as in experiment 1, but in which lime had been applied at the rate of 2 t/ha. Entries sown in both years were in one single row, 3 m long, 0.25 m between rows. Fang 60 or Sonora 64 were used as potential pollen donors on neighboring rows. Data showing male sterility responses are presented in Table 3 and Table 4. These tables show male sterility and grain set (Grain Set Index, %) in thirty wheat genotypes in a low B soil that had been limed (Table 3) and 25 genotypes (Table 4), respectively. Liming reduced grain set, that is, increased male sterility.

TABLE 3

Male sterility and grain set in wheat genotypes in a low B limed soil.

| Genotype[1] | Male sterility examination[2] Pollen staining with $KI/I_2$ (%) | Grain Set Index (%) Selfed (bagged) ± SE[3] |
|---|---|---|
| $U^2$K212B-4 | 0(A) | 0 |
| Sunelg | 0(A) | 0 |
| Bonza | 0(A) | 0 |
| Gamenya | 0(A) | 0 |
| Warrigal | 0(A) | 0 |
| QT5648 | 0(A) | 0 |
| Aroona | 0 | 0 |
| K113-A | 0(A) | 0 |
| RAC730 | 0(A) | 0 |
| Tatiara | 0(A) | 0 |
| Sundor | 20 | 0 |
| (YR10WARx)1/1 | 0 | 0 |
| SUN276A | 0(A) | 0 |
| K1182 | 0(A) | 0 |
| EL240 | 0 | 2 |
| Bd9 | 0 | 0 |
| Veery | 5 | 2 |
| Eradu | 0(A) | 2 ± 4 |
| Kenya Farmer | 0(A) | 2 ± 4 |
| ED089 | 0 | 2 ± 5 |
| BD135 | 10 | 7 ± 8 |
| WW1248 | 0(A) | 5 ± 11 |
| Gutha | 0(A) | 12 ± 16 |
| Benvenuto Inca | 10 | 23 ± 28 |
| G61450 | 30 | 32 ± 23 |
| Turkey 1473 | 70 | 58 ± 28 |
| SW41 | 15 | 11 ± 16 |
| Sonora 64 | 55 | 43 ± 47 |
| Fang 60 | 95 | 92 ± 5 |

(1) "F" designates potential father line and "M" potential mother line for producing hybrids.
(2) Anthers and pollen were examined after ear emergence. "A" in brackets designates anthers invisible or almost invisible to naked eyes in some florets.
(3) SE = standard error

TABLE 4

Male sterility and grain set in wheat genotypes in a low B limed soil.

| Genotype(1) | Male sterility/fertility examination(2) | Grain Set Index (%) |
|---|---|---|
| Fang 60 | fertile | 100 |
| Sonora 64 | fertile | 90 |
| CMU-F2* | fertile | 85 |
| CMU-F3 | fertile | 100 |
| CMU-F5 | fertile | 100 |
| CMU-F6 | fertile | 100 |
| CMU-F7 | fertile | 100 |
| CMU-F8 | fertile | 100 |
| Tatiara | sterile | 0 |
| Eradu | sterile | 0 |
| Warrigal | sterile | 0 |
| Gamenya | sterile | 0 |
| Halberd | sterile | 5 |
| Schombergk | sterile | 0 |
| BT Schombergk | sterile | 0 |
| Spear | sterile | 0 |
| Machete | sterile | 0 |
| Wilgoyne | sterile | 0 |
| Kite | sterile | 0 |
| Bonza | sterile | 0 |
| CMU-M12 | sterile | 0 |
| CMU-M23 | sterile | 0 |
| CMU-M24 | sterile | 0 |
| SW41* | partial-sterile | 28 |
| Tabuk* | partial-sterile | 36 |

(1) same as Table 3. * denotes standard check genotypes
(2) Fertile means anthers are of normal size, shape and color, and contain numerous pollen grains which mostly stain dark with iodine, and when flowering occurred the anthers split open to shed pollen. Sterile means anthers that are small, arrow shaped, do not shed pollen when flowering stage was reached, when the anthers are opened under microscope they were found to contain very few pollen grains, and the pollen grains were small, misshapen and do not stain with iodine, indicating that they are not viable.

Boron deficiency and male sterility were enhanced by liming. Many more genotypes become completely male sterile than in the low B but unlimed soil (cf. example 2, Table 2), including seven genotypes shown in both Tables 3 and 4. Fewer genotypes were completely male fertile in the limed soil. But selection from a wide range of germplasm yielded more potential pollen donors (e.g. CMU-F2, CMU-F3, CMU-F5, CMU-F6, CMU-F7, CMU-F8) which are tolerant to boron deficiency at the same level as Fang 60, a preferred standard pollen donor.

The morphology of the anthers and pollen of all the lines in Table 3 and Table 4 was studied under dissecting microscope, at 14× to 80× magnification. See FIG. 1. For Fang 60 anthers 2 were fertile as in FIG. 1E. Pollen grains were about twice the size for the following two lines, and they turn black in $KI/I_2$ solution as a result of reaction with starch deposits. For pollen of Eradu, there was no reaction with iodine in a KI/I solution, i.e. they are transparent, which helps to show they are empty. The anthers 5 were of the type shown in FIG. 1F. For Tatiara, anthers appeared as in sterile anthers 5 of the type shown in FIG. 1G. Few pollen grains were visible, and these were similar to Eradu.

EXAMPLE 4

Screening Wheat Genotypes in a Sand Culture

The sand culture consisted of earthenware pots, with 30 cm diameter and 30 cm deep, containing washed river sand with no detectable available boron. The pots were sown with 5–10 wheat plants per pot, and watered twice daily (morning and afternoon) with an otherwise complete nutrient solution (Table 5), in which the level of boron can vary from nil to 20 micromolar. Published accounts have shown that 0.5 micromolar of boron in the nutrient solution provide sufficient supply of boron for full fertility in wheat (Rerkasem and Loneragan 1994). Normally, 1 micromolar boron is used for adequate level of boron supply. In this environment, the amount of boron that was present as "impurities" in the chemical salts used to make up the nutrient solution and in the water supply was sufficient for vegetative growth but not enough to meet reproductive demand. This procedure was used to screen wheat genotypes for the purpose of selecting for tolerance to boron deficiency since 1990. But in the preferred embodiment of this invention the procedure is used to identify plants on the whole spectrum of sensitivity to boron deficiency, i.e. those that are extremely sensitive to boron deficiency (i.e. 100% male sterile) through to those that are that are extremely tolerant (i.e. 100% male fertile).

TABLE 5

Nutrient solution used in sand culture for screening wheat genotypes as to sensitivity to boron deficiency.

| Stock solution | Element | Salt | g/l |
|---|---|---|---|
| 1 | Ca | $CaCl_2.2H_2O$ | 294.1 |
| 2 | P | $KH_2PO_4$ | 136.1 |
| 3 | Fe | Fe-citrate | 6.7 |
|   | Mg | $MgSO_4.H_2O$ | 123.3 |
|   | K | $K_2SO_4$ | 87.0 |
|   | Mn | $Mn_2SO_4.H_2O$ | 0.338 |
| 4 | Zn | $ZnSO_4.7H_2O$ | 0.288 |
|   | Cu | $CuSO_4.5H_2O$ | 0.1 |
|   | Co | $CoSO_4.7H_2O$ | 0.056 |
|   | Mo | $Na_2MoO_2.2H_2O$ | 0.048 |
| 5 | N | $KNO_3$ | 101.0 |
| 6 | B | $H_3BO_3$ | 0.247 |

Boron free: for each liter of full strength nutrient solution, take 5 ml each of stock solutions 1, 2, 3, 4; plus 50 ml of solution 5, dilute to 10 liters with water.

Boron plus: add 5 ml of stock solution 6, 5 ml each of 1,2,3,4, and 50 ml of 5 to make 10 liters of nutrient solution having 2 micromolar boron in solution.

Source: Modified from Broughton and Dilworth (1971) Biochem. J. 125:1075–1080.

In Table 6, 33 genotypes were sown in sand culture with B at 0 and 1 micromolar, each level in duplicate plots. Each pot contained 10 plants. All genotypes were fertile and set grain normally in B+. The first five genotypes were male fertile and set grain normally in B0. The remaining 25 genotypes were male sterile and set no grain in B0 (Table 6). This table shows grain set (Grain Set Index, %) for 33 wheat genotype in a sand culture with (B+) and without (B0) added B.

TABLE 6

Grain set for wheat genotypes in sand culture with and without added B

| Genotype[1] | Grain Set Index (%) | |
|---|---|---|
|  | B0 | B+ |
| Fang 60 | 98 | 100 |
| CMU-F4 | 85 | 100 |
| CMU-F9 | 100 | 100 |
| CMU-F10 | 100 | 100 |
| CMU-F11 | 100 | 100 |
| CMU-M9 | 0 | 100 |
| CMU-M27 | 0 | 100 |
| (YR10WARx)1/1 | 0 | 94 |
| 82Y; 1185 | 0 | 100 |
| 84Z; 1156 | 0 | 98 |
| BD231 | 0 | 100 |
| Bd9 | 0 | 90 |

TABLE 6-continued

Grain set for wheat genotypes in sand culture with and without added B

| Genotype[1] | Grain Set Index (%) | |
|---|---|---|
|  | B0 | B+ |
| ED089 | 0 | 97 |
| ED135 | 0 | 98 |
| Egret | 0 | 93 |
| EL240 | 0 | 95 |
| K1182 | 0 | 96 |
| K11A-3 | 0 | 98 |
| QT4546 | 0 | 87 |
| QT4639 | 0 | 100 |
| QT5648 | 0 | 81 |
| RAC710 | 0 | 80 |
| RAC730 | 0 | 92 |
| SUN250c | 0 | 80 |
| SUN211A | 0 | 95 |
| SUN276A | 0 | 99 |
| Suneca | 0 | 85 |
| Sunelg | 0 | 98 |
| SW41 | 0 | 89 |
| Tatiara | 0 | 93 |
| $U^2$K212B-4 | 0 | 87 |
| Veery | 0 | 98 |
| WW1248 | 0 | 97 |
| Sundor | 5.5 | 99 |

(1) same as in Table 3

In Table 7, 14 genotypes were found to be completely sterile in the sand culture without added B, while Fang 60 was completely fertile (Table 7). Table 7 shows grain set (Grain Set Index, %) for 15 wheat genotypes in a sand culture without added B in the nutrient solution.

TABLE 7

Grain set for 15 wheat genotype in a sand culture without added B, exp. 4.2.

| Genotype | Male sterility/fertility examination‡ | Grain Set Index (%) |
|---|---|---|
| Fang 60 | fertile | 100 |
| Tatiara | sterile | 0 |
| Eradu | sterile | 0 |
| Warrigal | sterile | 0 |
| Gamenya | sterile | 0 |
| Halberd | sterile | 0 |
| Schombergk | sterile | 0 |
| BT Schombergk | sterile | 0 |
| Spear | sterile | 0 |
| Machete | sterile | 0 |
| Wilgoyne | sterile | 0 |
| Kite | sterile | 0 |
| SW41 | sterile | 0 |
| Tabuk | sterile | 0 |
| Bonza | sterile | 0 |

‡ same as Table 3.

EXAMPLE 5

Crossing a Male Sterile Wheat Plant with a Male Fertile Pollen Donor in the Same Fertility-Selective Media This example shows grain set in low boron media of male sterile lines in the presence of male fertile lines as potential pollen donors. Wheat genotypes were grown in the same way as described in example 2, 3, 4, with varying levels of male sterility, but each also had a male fertile genotype growing near by, e.g. in rows on both sides along the length of the row, at a distance of 0.25 m away, or in neighboring pots. When the potential mother (male sterile) and potential father were managed so that they flowered at the same time, a natural cross-fertilization occurred. In the male sterile plants (mothers), flowers that were bagged to ensure self fertilization set from no grain to a few grains, but flowers that were allowed opportunity to be cross-fertilized from the neighboring male fertile father set more grains (Tables 8, 9,10).

Thus, in fertility-selective media, wheat plants that are male sterile are readily cross-fertilized by those that are male fertile, if managed in such a way that they reach anthesis (flowering) at the same time.

Table 8 shows the effect of a boron depleted soil (same as example 2) on grain set in male sterile wheat plants allowed to cross-fertilize with neighboring male fertile plants (in this case the male fertile plants were Fang 60 or Sonora 64) compared with self fertilization (bagging prevented cross-fertilization).

When GSI of selfed plants is zero, or GSI of crossed plants is at least about 10% higher than GSI of selfed plants, this demonstrates hybridization according to the invention. Preferably the difference is at least about 20%, and most preferably at least about 30%. (SW41, EL240, Sundor, WW1248, Benvenuto Inca and G16450). It is also desirable that GSI of selfed plants be less than about 20% of GSI of crossed plants, and that the GSI of crossed plants be greater than about 30%. However, as many of the lines with small (<10%) difference between GSI of cross-pollinated plants and self-pollinated plants did not match their flowering period properly with that of the pollen doner, improved synchronization of flowering in the male sterile and male fertile plants by methods familiar to plant breeders would increase this difference.

TABLE 8

Grain set in male sterile wheat plants allowed to cross-fertilize with neighboring male fertile plants compared with self-fertilized plants

| Genotype of female parent | Grain set index (%) | |
| --- | --- | --- |
| | Cross-fertilization allowed (ears not bagged) | Self fertilized (ears bagged at emergence) |
| RAC730 | 17 | 0 |
| 84Z; 1156 | 17 | 0 |
| Tatiara | 6 | 1 |
| (YR10WARx)1/1 | 11.5 | 2.5 |
| Sunelg | 14.5 | 4.5 |
| Halberd | 26 | 12 |
| Gamenya | 34.7 | 13.3 |
| Eradu | 20 | 15 |
| SW41 | 56.5 | 19 |
| (WI*MMC)/W1/10 | 34 | 25 |
| EL240 | 54 | 25 |
| Spear | 53.7 | 27 |
| Kenya Farmer | 46.7 | 28 |
| QT4639 | 46 | 33 |
| Egret | 57 | 34.5 |
| Sundor | 65.7 | 35 |
| ED089 | 56 | 36.3 |
| SUN211A | 60.3 | 36.7 |
| WW1248 | 93 | 40 |
| ED135 | 58 | 41.5 |
| Warrigal | 63 | 42.5 |
| Benvenuto Inca | 76 | 48.3 |
| G61450 | 85 | 53 |
| RAC710 | 60.7 | 54.3 |
| Turkey 1473 | 66 | 68 |
| Aus4743 | 89.3 | 68.7 |

Table 9 shows the effects of a limed soil (same as example 3) on grain set in male sterile wheat plants allowed to cross-fertilize with neighboring male fertile plants (in this case the male fertile plants were Fang 60 or Sonora 64) compared with self-fertilized plants (bagging prevented cross-fertilization). Most preferred additional to those lines listed in Table 8 were Veery, 82Y;1185, Spear, RAC710, Egret, and Suneca.

TABLE 9

Grain set in male sterile wheat plants cross-fertilized with neighboring male fertile plants or self-fertilized.

| Genotype of female parent | Grain set index (%) | |
| --- | --- | --- |
| | Cross-fertilization allowed (ears not bagged) | Self fertilized (ears bagged at emergence) |
| CMU-M17 | 32 | 1 |
| CMU-M21 | 18 | 2 |
| K1182 | 6 | 0 |
| QT5648 | 0 | 0 |
| Aroona | 2.5 | 0 |
| RAC730 | 0 | 0 |
| Bd9 | 26 | 0 |
| 84Z; 1156 | 0 | 0 |
| K11A-3 | 0 | 0 |
| Warrigal | 0 | 0 |
| $U^2$K212B-4 | 0 | 0 |
| Sundor | 1.5 | 0 |
| Gamenya | 0 | 0 |
| Tatiara | 5 | 0 |
| (YR10WARx)1/1 | 7 | 0 |
| Sunelg | 0 | 0 |
| Bonza | 2 | 0 |
| QT4639 | 2 | 0.5 |
| Eradu | 2 | 1 |
| EL240 | 11.5 | 1 |
| SUN276A | 12.5 | 1.5 |
| Kenya Farmer | 2.5 | 1.5 |
| Veery | 35 | 2 |
| SUN211A | 23 | 2 |
| ED089 | 0 | 2.5 |
| WW1248 | 1 | 5.5 |
| Lin Calel | 18 | 7 |
| ED135 | 9 | 7 |
| Kite | 17 | 8 |
| 82Y; 1185 | 41.5 | 9.5 |
| Aus4743 | 29 | 10.5 |
| Spear | 45.5 | 11.5 |
| Benvenuto Inca | 47 | 11.5 |
| Gutha | 29 | 12 |
| Hartog | 19 | 13.5 |
| SW41 | 51.5 | 16.5 |
| RAC710 | 45.5 | 18 |
| Halberd | 16 | 20 |
| Egret | 81.5 | 26 |
| G61450 | 83 | 32.5 |
| SUN250c | 14.5 | 33 |
| Turkey 1473 | 79.5 | 59 |
| Suneca | 92 | 63 |

Table 10 shows the effects of boron-free sand culture (man-made medium, same as example 4) on grain set in male sterile wheat plants allowed to cross-fertilize with pollen from neighboring male fertile plants (in this case genotypes of the male fertile plants were not determined, as there were male fertile plants of various genotypes in proximity) compared with self-fertilized plants (bagging prevented cross-fertilization). All of these lines are appropriate mother plants because no selfing occurred.

TABLE 10

Grain set in male sterile wheat plants grown in sand culture and allowed to cross fertilize with neighboring male fertile plants compared with self fertilized plants.

| Genotype of female parent | Grain set index (%) Cross-fertilization allowed (ears not bagged) | Self fertilized (ears bagged at emergence) |
|---|---|---|
| CMU-M29 | 76 | 0 |
| CMU-M30 | 67 | 0 |
| EL 240 | 8 | 0 |
| ED089 | 13 | 0 |
| QT4639 | 15 | 0 |
| ED135 | 36 | 0 |
| Egret | 42 | 0 |
| Veery | 25 | 0 |
| K11A-3 | 63 | 0 |
| RAC710 | 41 | 0 |

EXAMPLE 6

Enhancement of Grain Set in Male Sterile Female Parent Plants with an Application of Boron to the Ear of the Female Parent Wheat plants grown in the same condition as in example 5 (boron depleted soil, limed soil, sand culture) were manually cross-fertilized with pollen from the male fertile Fang 60. Grain set was compared for a spraying of a 0.05% boric acid solution (w/v) on the ear of the female parent, and a spraying without boron (Table 11, boron depleted soil; and Table 12, limed soil; Table 13 in sand culture without added B).

The stigmas of male sterile plants received either deionized water (control), or a micronutrient spray containing boric acid at pollination with a donor pollen. As shown in the tables, when micronutrient spray is applied to wheat ears at pollination, the percentage of florets set (i.e. percentage of florets crossed that set seed) increases dramatically, from about two to ten fold, depending on the wheat line tested. The wheat lines $U^2K212B-4$, Lin Calel, QT4546, 82Y;1185, SMGBW88001, Sunelg, and Eradu, each of which was 100% male sterile when grown in low boron soil, set seed in approximately 12% to 50% of florets following stigma pretreatment. These data indicate that in a method according to the invention, grain set of male sterile plants grown in fertility-selective media is significantly improved by using a stigma pretreatment comprising a micronutrient spray, in conjunction with manual pollination from a pollen donor.

TABLE 11

Enhancing grain set with boric acid application to the ear of male sterile female plants in boron depleted soil

| Genotype of female parent | Without Boric acid solution spray | | | With Boric acid solution spray | | |
|---|---|---|---|---|---|---|
| | Florets crossed | Grains set | % grain set | Florets crossed | Grains set | % grain set |
| CMU-M31 | 61 | 9 | 14.7 | 51 | 17 | 33.3 |
| CMU-M18 | 90 | 16 | 17.8 | 120 | 40 | 33.3 |
| CMU-M28 | 150 | 31 | 21.7 | 100 | 46 | 46.0 |
| Lin Calel | 71 | 0 | 0 | 54 | 14 | 25.9 |
| RAC710 | 61 | 3 | 4.9 | 93 | 44 | 47.3 |
| ED089 | 71 | 4 | 5.6 | 42 | 6 | 14.3 |
| Sundor | 84 | 6 | 7.1 | 41 | 10 | 24.4 |

TABLE 11-continued

Enhancing grain set with boric acid application to the ear of male sterile female plants in boron depleted soil

| Genotype of female parent | Without Boric acid solution spray | | | With Boric acid solution spray | | |
|---|---|---|---|---|---|---|
| | Florets crossed | Grains set | % grain set | Florets crossed | Grains set | % grain set |
| ED135 | 70 | 9 | 12.9 | 66 | 36 | 54.6 |
| EL240 | 107 | 11 | 10.3 | 72 | 34 | 47.2 |
| Egret | 96 | 38 | 39.6 | 140 | 90 | 64.3 |

TABLE 12

Enhancing grain set with an application of boric acid to the ear of male sterile female parent plants growing on limed soil.

| Genotype of female parent | Without Boric acid solution spray | | | With Boric acid solution spray | | |
|---|---|---|---|---|---|---|
| | Florets crossed | Grains set | % grain set | Florets crossed | Grains set | % grain set |
| QT4546 | 63 | 0 | 0.0 | 25 | 3 | 12.0 |
| $U^2K212B-4$ | 125 | 0 | 0.0 | 111 | 26 | 23.4 |
| Lin Calel | 71 | 0 | 0.0 | 54 | 14 | 25.9 |
| Sunelg | 119 | 0 | 0.0 | 106 | 38 | 35.8 |
| 82Y; 1185 | 54 | 0 | 0.0 | 86 | 34 | 39.5 |
| Eradu | 27 | 0 | 0.0 | 50 | 23 | 46.0 |
| SUN276A | 161 | 1 | 0.6 | 104 | 1 | 1.0 |
| 84Z; 1156 | 46 | 1 | 1.6 | 44 | 3 | 6.8 |
| Warrigal | 102 | 1 | 1.0 | 99 | 17 | 17.2 |
| Gamenya | 96 | 1 | 1.0 | 96 | 25 | 26.0 |
| Kite | 126 | 1 | 0.8 | 33 | 22 | 66.7 |
| Spear | 68 | 3 | 4.4 | 60 | 22 | 36.7 |
| WW1248 | 66 | 3 | 4.5 | 66 | 29 | 43.9 |
| RAC710 | 61 | 3 | 4.9 | 93 | 44 | 47.3 |
| ED089 | 71 | 3 | 4.2 | 42 | 6 | 14.3 |
| Tatiara | 119 | 4 | 3.4 | 149 | 47 | 31.5 |
| Halberd | 72 | 4 | 5.6 | 72 | 36 | 50.0 |
| Sundor | 84 | 6 | 7.1 | 41 | 10 | 24.4 |
| Bonza | 90 | 6 | 6.7 | 100 | 37 | 37.0 |
| (YR10WARx) 1/1 | 62 | 9 | 14.5 | 75 | 25 | 33.3 |
| ED135 | 101 | 9 | 8.9 | 66 | 36 | 54.5 |
| Kenya Farmer | 68 | 10 | 14.7 | 90 | 30 | 33.3 |
| EL240 | 107 | 11 | 10.3 | 72 | 34 | 47.2 |
| G61450 | 55 | 12 | 21.8 | 47 | 19 | 40.4 |
| Benvenuto Inca | 75 | 29 | 38.7 | 113 | 56 | 49.6 |
| SW41 | 72 | 21 | 29.2 | 73 | 43 | 58.9 |
| SUN211A | 148 | 33 | 22.3 | 154 | 74 | 48.1 |
| Egret | 96 | 38 | 39.6 | 140 | 90 | 64.3 |
| Aus4743 | 98 | 38 | 38.8 | 93 | 64 | 68.8 |
| Turkey 1473 | 57 | 47 | 82.5 | 104 | 67 | 64.4 |

TABLE 13

Enhancing grain set with an application of boric acid to the ear of male sterile female parent plants growing in sand culture without added B.

| Genotype of female parent | Without Boric acid solution spray | | | With Boric acid solution spray | | |
|---|---|---|---|---|---|---|
| | Florets crossed | Grains set | % grain set | Florets crossed | Grains set | % grain set |
| SMGBW88001 | 28 | 0 | 0 | 60 | 34 | 56.7 |
| SW41 | 88 | 11 | 11.4 | 90 | 29 | 32.2 |
| Kalyasona | 114 | 17 | 14.9 | 154 | 61 | 39.6 |
| BL1022 | 24 | 4 | 16.7 | 48 | 18 | 37.5 |
| Kanchan | 108 | 19 | 17.6 | 122 | 54 | 44.3 |

EXAMPLE 7

Male Fertility in Low B of F1s Compared with their Respective Female Parents Seeds of fourteen of F1s from crosses with Fang 60 as the male parent were sown in a low B soil that had been limed (as in example 3). All of the female parents were sensitive to B deficiency to the extent that there were all male sterile, set virtually no grain when selfed (bagged) in the limed soil. The least sensitive amongst the female parent was SW41, which had Grain Set Index of 27.5% in the limed soil. With Fang 60 as male parent, nine of the F1s were much more tolerant to B deficiency than their respective female parents, showing none of the symptoms of male sterility (i.e. anthers and pollen normal, no gaping florets) and set grain normally. Five of the F1s, however, exhibited all of the symptoms of male sterility (100% florets gaping at anthesis) and set no grain. (Table 14).

TABLE 14

Male fertility and grain set in F1s with Fang 60 as the male parent.

| Female parent | Female parent male fertility | F1 (male parent: Fang 60) | |
|---|---|---|---|
| | | Male fertility | Grain set index in low B (%) |
| Veery | sterile | fertile | 95 |
| Sunelg | sterile | fertile | 100 |
| 84Z; 1156 | sterile | fertile | 96 |
| K11A-3 | sterile | fertile | 100 |
| U$^2$K212B-4 | sterile | fertile | 85 |
| SUN211A | sterile | fertile | 90 |
| 82Y; 1185 | sterile | fertile | 100 |
| RAC730 | sterile | fertile | 100 |
| SW41 | sterile | fertile | 97.5 |
| Tatiara | sterile | sterile | 0 |
| (W1xMMC)/W1/10 | sterile | sterile | 0 |
| EL240 | sterile | sterile | 0 |
| Kenya Farmer | sterile | sterile | 0 |
| Warrigal | sterile | sterile | 0 |

Thus, in fertility-selective media, some F1s, with Fang 60 as the male parent (pollen donor) were fully male fertile, compared with respective female parents which were male sterile. Such F1 plants may then be used as male parents for multiple crosses.

EXAMPLE 8

Selecting Female and Male Parent Lines for a Self-Pollinating Species in a Micronutrient-Deficient Growth Medium A self-pollinating species is screened to select for female and male parent lines that are male fertility-sensitive and female fertility-tolerant, or male fertility-tolerant, respectively, in a fertility-selective growth medium having a concentration of a selected micronutrient that is reduced from the normal growth requirements for the species. First, the fertility-selective media are identified by growing in them a number of lines of the species with known fertility/sterility responses. The media that are evaluated cover a range of availability of the micronutrient that is likely to give the desired responses in that particular species. Appropriate media are those that give the "largest possible" or "predetermined" difference in fertility/sterility between the tolerant and sensitive lines of the standard checks. Ears are examined for anther "health" and pollen viability and bagged to prevent cross-pollination.

For boron, the levels of boron are 0.0, 0.1, 0.2, 0.5, 1.0 and 2.0 micromolar boron, or alternatively a soil with lowest possible available boron that can be found, e.g. 0.12 mg HWSB/kg, with lime application at 0, 500, 1,000 and 2,000 kg/ha. For manganese and corn, the levels are 0.0, 0.05, 0.1, 0.2, 1.0,10.0 micromolar manganese.

Once the fertility-selective medium is selected, seeds from a variety of lines are planted, preferably with another set in complete nutrient sufficiency, or "normal" medium as checks. Plants are then raised and tested for male fertility and female fertility. Flowers are bagged to exclude cross-pollination. Those lines that have a substantially reduced grain set in the micronutrient-deficient growth medium (as compared to the normal medium) are tested further by observation of male flower parts and pollen staining to identify those that lack viable pollen. Lines that are male sterile under these conditions are tested for female fertility by crossing with a male fertile plant (one that is raised in normal growth medium or one that is male fertility-tolerant in a micronutrient-deficient medium). Lines whose grain set is significantly higher than in the bagged cross are selected as female parents (female fertile, male sterile). Female plants with low grain set may receive a spray containing the micronutrient before pollination to enhance female fertility. These lines are female fertility-tolerant and male fertility-sensitive to the micronutrient-deficient medium. Male parent lines are selected as those that are male fertility-tolerant to a particular level of micronutrient deficiency. Screening is done by microscopic examination, pollen staining, determining self-pollination by grain set when bagged, or other accepted methods.

Then, female and male parent lines are selected with a growth medium having a particular degree of deficiency for a micronutrient, and the female and male plants are raised and crossed to produce seeds for F1 hybrid plants.

EXAMPLE 9

This and the following examples relate to the particular embodiment involving measurement of boron levels in male sexual organs. Two wheat genotypes, Fang 60 and SW41 were grown in a soil (loamy sand, series Sansai) containing hot water soluble boron (HWSB) at 0.14 mg kg$^{-1}$, with 4 levels of lime, at 0, 1500, 3000, and 6000 kg per hectare in four replicates. At ear emergence, 20 ears in each plot were bagged to ensure self pollination, 50 other ears were sampled for boron analysis (Loshe, 1982) of the male reproductive organs (anthers, containing pollen grains). The anthers were dried in a ventilated oven at 80° C. for 48 hours, dry ashed and the amount of boron determined spectrometrically after developing a colour with Azomethine-H, by the method of Loshe 1982. The level of male fertility was determined as Grain Set Index, % (Rerkasem and Loneragan, 1994) in the self pollinated ears. The relationships between male fertility (% Grain Set Index by self pollination) and boron contents of the anthers are shown in Table 15. Anthers of Fang 60 appeared normal in all lime treatments. Male sterility in SW41 was indicated by flowers that remained open for several days during anthesis, pollen grains that appeared dented like deflated footballs and did not stain with iodine (Rerkasem et al., 1989). With no lime SW41 exhibited no symptom of male sterility. With lime at 1,500 kg per hectare, a few ears showed symptoms of male sterility, and the intensity of male sterility symptoms increased with increasing lime rate.

TABLE 15

The control of male fertility (% Grain Set Index in self pollinated ears) by controlling boron contents of the anthers in two wheat genotypes.

| | Wheat genotype: Fang 60 | | Wheat genotype: SW41 | |
|---|---|---|---|---|
| kg ha$^{-1}$ | Boron in anthers (mg B kg$^{-1}$) | Grain Set Index* (%) | Boron in anthers (mg B kg$^{-1}$) | Grain Set Index (%) |
| 0 | 12 | 97 | 12 | 88 |
| 1500 | 11 | 98 | 10 | 75 |
| 3000 | 11 | 98 | 9 | 62 |
| 6000 | 11 | 99 | 8 | 55 |

*by self pollination.

Wheat plants are generally considered completely fertile with Grain Set Index >85%. As it was able to concentrate 11 mg B kg$^{-1}$ or more in its anthers, the wheat genotype Fang 60 was always fully fertile. The level of B in the anthers of the genotype SW41, on the other hand, decreased with decreasing level of male fertility, with the result in decreasing self fertility, to a Grain Set Index of only 55% with 8 mg B kg$^{-1}$ in the anthers.

EXAMPLE 10

Fang 60 plus 10 other genotypes of wheat (Gamenya, Tatiara, Kite, Machete, Spear, Bonza, Eradu, Warrigal, Wilgoyne, SW41) were grown in a soil (loamy sand series Sansai) containing 0.11 mg HWSB kg$^{-1}$, which had been limed at the rate of 2000 kg per ha. At ear emergence, 20 ears in each plot were bagged to ensure self pollination, 50 other ears were sampled for boron analysis (Loshe, 1982) of the male reproductive organs (anthers, containing pollen grains). Some anthers and the pollen grains were also examined under microscope, with KI/I$_2$ staining of pollen grains to check starch contents. The level of male fertility was determined as Grain Set Index, % (Rerkasem and Loneragan, 1994) in the self pollinated ears. The relationships between male fertility (% Grain Set Index by self pollination) and boron contents of the anthers are shown in Table 16.

TABLE 16

Controlling self fertility in 11 wheat genotypes by controlling boron content of the anthers.

| Genotype | Appearance of anthers and pollen | Boron in anthers (mg B kg$^{-1}$) | Grain Set Index$^{-1}$ (%) |
|---|---|---|---|
| Fang 60 | Fertile | 12.2 ± 1.1 | 95.2 ± 5.2 |
| Means of 10 genotypes[2] | Sterile | 5.5 ± 1.2 | 5.1 ± 8.5 |

[1]By self fertilisation.
[2]Including Gamenya, Tatiara, Kite, Machete, Spear, Bonza, Eradu, Warrigal, Wilgoyne, SW41.

In the ten wheat genotypes that contained 5.5±1.1 mg B kg$^{-1}$ Set Index averaged 5.1±8.5%. They all had male reproductive organs (anthers and pollen grains) that were visibly sterile. In many of their florets the anthers were shrivelled and small (<0.5 mm to almost invisible with naked eye). In these anthers, pollen grains were few (<100 vs normally >1,000), small (<½ normal size), when examined under microscope they appear empty, transparent and misshapen (like deflated footballs) and did not stain with iodine. All of these are indications of male sterility. In comparison, Fang 60 with 12.2±1.1 mg B kg$^{-1}$ in the anthers was completely fertile.

Hybridisation was successfully made with Fang 60 which contained >11 mg B kg$^{-1}$ in the anthers and completely male fertile as the male parent with female parents with about 6 mg B kg$^{-1}$ in the anthers that were male sterile without any need for manual emasculation or other method for controlling male sterility.

EXAMPLE 11

Figure 3:
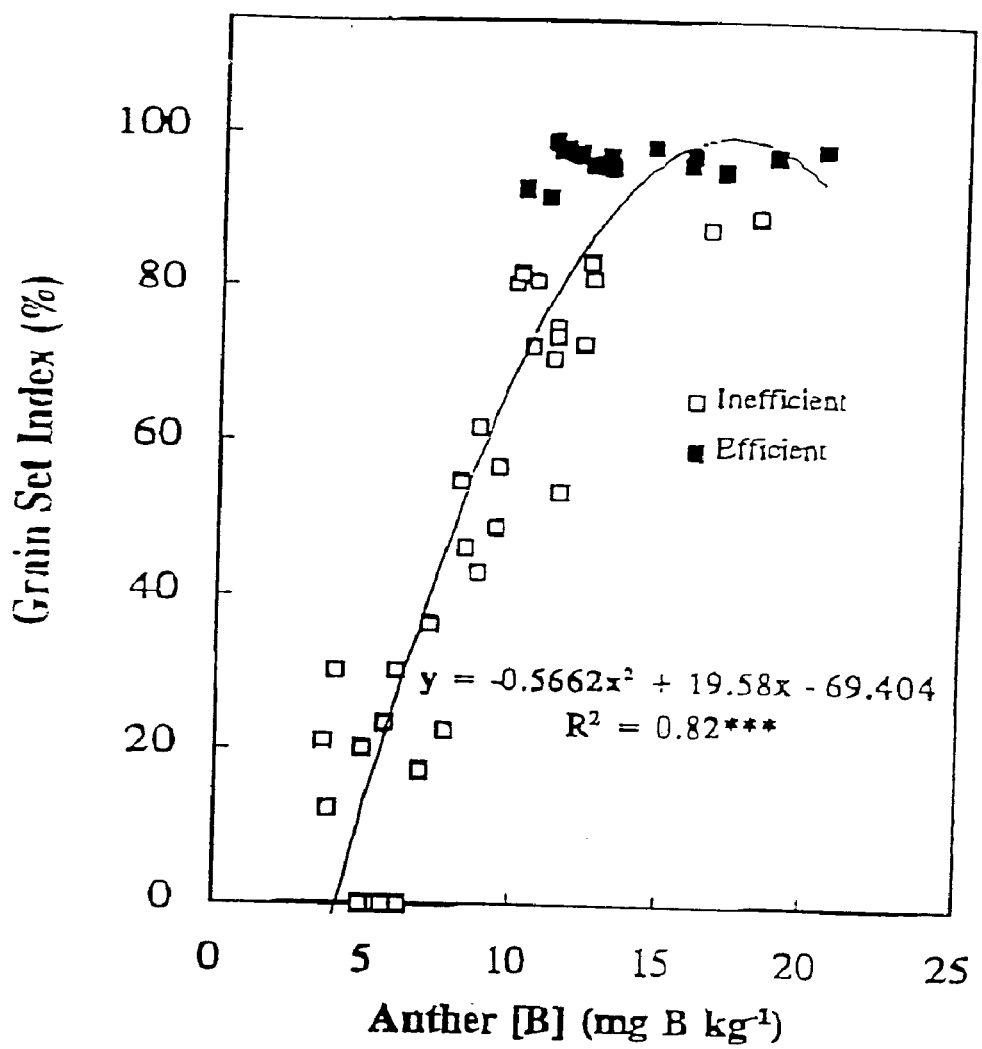
FIG. 3 illustrates the relationship between Grain Set Index when self-fertilized and anther B for wheat genotypes with different levels of anther B capacity. Those with low anther B capacity (inefficient) are represented by open squares, and high anther capacity (efficient) by solid squares.

The relationship between anther B concentrations and Grain Set Index when self-fertilized has been established for wheat (FIG. 3). The data came from examples 9 and 10 plus additional data from an experiment in which wheat genotypes were grown at four levels of soil B (ranging from 0.1–0.2 mg hot water soluble B kg–1), over two seasons, in four replications. Fang 60 represented the wheat genotype with high anther B capacity (designated "efficient"). The genotypes with low anther B capacity (designated "inefficient") were represented by SW41, Gamenya, Tatiara, Kite, Machete, Spear, Bonza, Eradu, Warrigal and Wilgoyn.

FIG. 3 illustrates the relationship between anther boron content and Grain Set Index in self fertilized wheat. The relationship is described by a fitted equation Y=−0.5662X2+19.58X−69.404 (R2=0.82), where Y is the Grain Set Index when self fertilized, and X is B concentration in the anthers (mg B kg–1 dry weight at ear emergence). Each data point is mean of two to four replicates. Solid squares designate data from wheat plants of genotype that are able to transport high levels of boron into their anthers (labelled "efficient") and open squares designate data from wheat plants of genotypes that are less able to transport less boron into their anthers (labelled "inefficient"). The resulting curve or the fitted equation maybe used to predict the level of male sterility to the expected for a given level of anther boron. In FIG. 3 for an inefficient strain at anther boron of 7 mg/kg, Grain Set Index would be expected to be about 40%.

EXAMPLE 12

The effect of boron (B) deficiency on reproductive development was examined in a wheat line SW41 at 4 B levels in a field experiment. The soil B levels (designated BO, B1, B2, B3) ranged from 0.1 to 0.2 mg hot water soluble B kg$^{-1}$. No effect on vegetative growth was detected at any of the B levels, but the number of grains ear$^{-1}$ increased with B, from 7 in BO to 21 in B3; and Grain Set Index (GSI) also increased from 22% to 60%. At ear emergence, B content (mg B kg$^{-1}$ DW) of the ear ranged from 2.2 to 3.1 and of the flag leaf from 4.1 to 4.7, but these bore slight to no relationship to the number of grains ear$^{-1}$ or GSI. Higher B concentrations were found in the anthers; more significantly, grain set was closely correlated with B in the anthers (R$^2$ 0.77). The significant correlation between Grain Set Index and anther B was confirmed with a larger set of data. With 7 mg B kg–1 DW in the anthers, the number of grains ear$^{-1}$ was doubled when cross pollination with B deficiency tolerant Fang 60 growing near by was allowed. In ears with 9 mg B kg$^{-1}$ in the anthers the effect of cross pollination was smaller, but significant.

Wheat plants of several genotypes growing in more severe B deficiency than BO had poorly developed anthers (small, <0.5 mm in length; shrivelled, sometime almost absent) and pollen (few, <100 anther$^{-1}$; about half normal size, empty and did not stain I$^2$) and set no grain when cross pollination was prevented by ear bagging. B contents of these plants at ear emergence were 4.2±0.8 mg B kg$^{-1}$ DW in the carpel, 5.1±1.0 in the anthers, 1.7±0.7 in the remainders of the ear (glumes, rachis, etc.), 2.9±0.6 in the flag leaf, and 2.6±0.9 in the first internode subtending the ear. Cross pollinated with healthy pollen, a few grains were set in these completely male sterile plants, but up to six times more when a B spray (boric acid 0.05%, w/v) was applied to the ear before fertilization.

Reproductive development in wheat requires more B than vegetative growth. While B deficiency depresses both male and female fertility, the effect on the anthers and pollen are more severe. The effect of B deficiency on the female part of the flower was also reversible, as grain set by cross pollination was enhanced by a B spray.

Materials and Methods

A low B sensitive wheat line SW41 (Rerkasem and Loneragan, 1994) was grown in the field at 4 B levels in four replicates. The soil B levels (designated B0, B1, B2, B3, and with hot water soluble B, HWSB, ranged from 0.1 to 0.2 mg $kg^{-1}$) had been previously established by different rates of borax application. Each replicate of each B level was 3 m wide and 10 m long, and SW41 was sown in six ten-meter rows, 0.25 m apart, accompanied by six-ten meter rows of Fang 60, a low B tolerant genotype. At ear emergence 50 randomly selected areas were sampled from each plot and analyzed for B separately as anthers (filaments may or may not be included), carpel (style and ovary), the remainders of the ear (chaff: glumes, rachis) and the flag leaf, and up to 100 ears were bagged to prevent cross-pollination. At maturity Grain Set Index (Rerkasem and Loneragan 1994) was determined on these 100 bagged ears. Seed yields were determined from harvested areas of 1 $m^2$ each of unbagged ears. A larger set of data on anther and carpel B and Grain Set Index of SW41 was obtained from two additional experiments. One was a long term experiment with four levels of B (0, 0.5, 1.0 and 2.0 kg B $ha^{-1}$) that had been applied to different plots in 1989, 1990 and 1991 (Rerkasem and Loneragan, 1994). The other involved 5 lime rates (0 to 4 t $ha^{-1}$) to vary the level of plant available B in a soil that originally had 0.14 mg HWSB $kg^{-1}$. Both experiments were in four replicates.

Six wheat genotypes classified as very sensitive to low B were sown in sand culture with no added B in the nutrient solution (Rerkasem and Loneragan, 1994) and also in the field on the same soil as B0 above that had received 2 t $ha^{-1}$ of hydrated quick lime to accentuate B deficiency. Separate B analyses were carried out for anthers, carpel, chaff, flag leaf and internode immediately below the ear for field grown plants at ear emergence. At maturity Grain Set Index was determined on ears that had been left unbagged and those that were bagged at ear emergence. Ten ears each were also cross pollinated with pollen from Fang 60 with an application of a B spray (boric acid 0.05%, w/v) 1-2 days before fertilization.

Results and Discussion

Boron deficiency depressed seed yield of SW41 wheat without apparently affecting straw yield, number of ears per meter, and average size of the ear (Table 17).

TABLE 17

Effects of soil B levels on yields and yield attributes in SW41 wheat.

| Soil B level | Seed yield[a] (kg $ha^{-1}$) | Straw yield (kg $ha^{-1}$) | Ears $m^{-2}$ | Spikelets $ear^{-1}$ | Florets[b] $spikelet^{-1}$ |
|---|---|---|---|---|---|
| B0 | 687 | 1857 | 170 | 14.6 | 3.4 |
| B1 | 630 | 1784 | 179 | 14.3 | 3.5 |
| B2 | 1138 | 1720 | 179 | 13.9 | 3.1 |
| B3 | 1375 | 1693 | 169 | 15.2 | 3.1 |

TABLE 17-continued

Effects of soil B levels on yields and yield attributes in SW41 wheat.

| Soil B level | Seed yield[a] (kg $ha^{-1}$) | Straw yield (kg $ha^{-1}$) | Ears $m^{-2}$ | Spikelets $ear^{-1}$ | Florets[b] $spikelet^{-1}$ |
|---|---|---|---|---|---|
| Significant difference ($p < 0.05$) | 127 | NS | NS | NS | NS |

[a]seed yield from unbagged ears
[b]competent florets

The number of grains $ear^{-1}$ and Grain Set Index were also depressed by B deficiency (Table 18).

TABLE 18

Effect on soil B levels on the number of grains $ear^{-1}$, Grain Set Index and B contents of wheat tissues.

| | Grain Set Index (%) | | Grains $ear^{-1}$ | |
|---|---|---|---|---|
| Soil B level | Bagged | Unbagged | Bagged | Unbagged |
| B0 | 22.3 | 41.3 | 7.0 | 11.8 |
| B1 | 36.3 | 60.8 | 9.8 | 19.5 |
| B2 | 46.4 | 72.4 | 15.2 | 23.2 |
| B3 | 59.7 | 77.4 | 21.4 | 25.6 |
| SE | 6.1 | | 3.5 | |

The depression of grain number and Grain Set Index by B deficiency was greater in those ears in which self pollination was forced by bagging (Table 4). The difference between bagged and unbagged ears varied with soil B ($p<0.05$), being largest in the intermediate B levels (B1 and B2) and larger in the highest (B3) and lowest (B0) levels. This together with the fact that bagging has no effect on grain number and Grain Set Index in B sufficient wheat (data not shown), indicates that the lower grain number and grain set in bagged ears really reflects the effect of B deficiency on male sterility and self fertilization and not just an artifact of bagging. As it was derived from samples of unbagged ears, cross-pollination would have contributed to half of the seed yield at certain levels of B deficiency.

The SW41 wheat in this study had 4-5 mg B $kg^{-1}$ in the flag leaf and 2-3 mg B $kg^{-1}$ in the whole ear, but there was no distinguishable difference between soil B levels from B0 to B3 on the concentration in these tissues (Table 19).

TABLE 19

Effects of soil B levels on B contenst of vegetative and reproductive tissues of wheat at ear emergence.

| Treatment | Flag leaf B | Ear B | Anthers B |
| | | mg B $kg^{-1}$ | |
|---|---|---|---|
| B0 | 4.7 | 2.2 | 7.5 |
| B1 | 4.1 | 2.5 | 7.0 |
| B2 | 4.4 | 3.1 | 8.3 |
| B3 | 4.5 | 2.9 | 9.4 |
| SE | 0.6 | 0.4 | 1.0 |

There was also no correlation between the flag leaf and ear B and the number of grains per ear and Grain Set Index. This study found much more B concentrated into the anthers than in the whole ear (Table 5). The whole ear averaged 2-3 mg B $kg^{-1}$, and the anther 7-9 mg B $kg^{-1}$. More significantly, there was a close correlation ($p<0.05$) between the number of grains $ear^{-1}$ and Grain Set Index and B concentration in the anthers ($R^2$ 0.77). The relationship between anther B and Grain Set Index remained consistently significant in a larger set of data (p<0.05). The critical deficiency content (CDC, Marschner 1995) of B for grain set was determined at 8 mg B kg$^{-1}$ for the carpel and 10 mg B kg$^{-1}$ for the anthers. These values have clearly established that the B requirement for reproductive tissues of wheat is higher than the vegetative requirement. Being enclosed in the glumes and leaf sheath for most of their development, the anthers and glumes are internal tissues with low transpiration, which would be somewhat limiting to their B supply via the xylem. Although direct evidence is still lacking, the situation of high requirement being unmet because of limited supply is a likely explanation for frequent incidences of B deficiency-induced sterility in wheat in the field.

Complete male sterility was observed in wheat genotypes classified as very sensitive to low B grown in low B soil that had been limed. They had poorly developed anthers (small, <0.5 mm in length; shrivelled, sometimes almost absent) and pollen (few, <100 anther$^{-1}$; about half normal size, empty and did not stain with $I_2$) and set no grain when cross-pollination was prevented by ear bagging (Table 20).

TABLE 20

Grain set and tissue B contents in wheat genotypes grown in a condition of low B soil that induced 100% male sterility. (± Standard Error)

| Natural pollination | Grain Set Index (%) |
|---|---|
| Bagged ears | 0 |
| Unbagged ears | 18 ± 15 |
| Manual pollination | Grain set (% florets with grain) |
| Without B | 25 ± 14 |
| With B$^a$ | 54 ± 27 |
| Tissue | B contents (mg B kg$^{-1}$) |
| Anther | 5.1 ± 14 |
| Carpel | 4.2 ± 0.8 |
| Chaff | 1.7 ± 0.7 |
| Flag leaf | 2.9 ± 0.6 |
| Peduncle | 2.6 ± 0.9 |

$^a$A spray of B solution (boric acid 0.05%, w/v) applied to the ear 1–2 days before fertilization.

B contents of these plants at ear emergence were 4.2±0.8 mg B kg$^{-1}$ DW in the carpel, 5.1±1.0 in the anthers, 1.7±0.7 in the remainders of the ear (glumes, rachis). 2.9±0.6 in the flag leaf, and 2.6±0.9 in the peduncle, first internode subtending the ear. When these completely male sterile plants were cross-pollinated with healthy pollen, some grains were set, and six times more when a B spray (boric acid 0.05%, w/v) was applied to the ear 1–2 days before fertilization. The response of grain set to cross-pollination and the lower CDC of B for carpel together suggest a lower requirement for B than the anthers. The actual B requirement of the female gamete could be even lower than is reflected by the apparent CDC of B for the carpel. External B requirement for pollen germination has been demonstrated in wheat (Cheng and Rerkasem 1993) and other species (Vaughan 1977; Dickinson 1978). The apparent CDC for the carpel and the grain set response to B spray may well be reflecting the requirement for external B that is normally supplied in the stigma and style instead of the requirement of the female gamete as such.

Reproductive development in wheat requires more B than vegetative development. The B requirement of the male reproductive organs of the anthers is also greater than that of the female organs. This requirement, previously unrecognized, may be used to select parent plants suitable for hybridizing at a given level of boron.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A method for producing hybrid seeds comprising:
   (a) providing a fertility-selective growth medium having a deficiency for a micronutrient, wherein the micronutrient is boron;
   (b) selecting from a plant species that is normally self-pollinating parents having different genotypes consisting of a female plant and a male plant, the plant being wheat,
      (i) the female plant having a phenotype of female fertility tolerance and male fertility sensitivity to the micronutrient deficiency, such that the plant does not produce normal pollen but has female fertility; and
      (ii) the male plant having a phenotype of male fertility tolerance to the micronutrient deficiency, and producing normal pollen;
   (c) growing the female plant to sexual maturity in the fertility-selective growth medium to produce a plant having female fertility and male sterility;
   (d) growing the male plant to sexual maturity to produce a plant having male fertility;
   (e) cross-pollinating the female plant with pollen from the male plant to produce cross-fertilization;
   (f) raising the female plant to produce hybrid seeds having genetic material from both parents; and
   (g) harvesting the hybrid seeds.

2. The method of claim 1 further comprising raising a hybrid plant from the hybrid seed.

3. The method of claim 1, further comprising the steps of cultivating the hybrid seed to produce a hybrid plant, and crossing the hybrid plant with a plant having a different genotype to produce a three-way cross.

4. The method of claim 3 wherein the hybrid plant has a phenotype of male sterility and female fertility when grown in a micronutrient-deficient environment, and the further crossing step comprises crossing the hybrid with a male plant having a different genotype.

5. The method of claim 3, further comprising raising a hybrid female plant with a phenotype of male sterility in a fertility-selective medium, and a hybrid male plant with a phenotype of male fertility, and crossing the hybrid male and female plants in a fertility-selective growth medium to produce a quadruple-cross.

6. The method of claim 1 further comprising raising the male and female together in the same growth medium and allowing cross-pollination to take place without manual assistance.

7. The method of claim 1 wherein the level of micronutrient in the growth medium available to the plant is almost nil.

8. The method of claim 1, wherein the female parent's sensitivity to the deficiency is greater in the male parts of the flowers than the female parts and greater in the reproductive male parts than the non-reproductive male parts, such that the deficiency causes morphological effects producing male sterility while retaining female fertility.

9. The method of claim 1, wherein when self-pollinated, the female parent has a grain set which is less than about 20% of that for a selfed isogenic plant grown under the same conditions but without micronutrient deficiency, and when cross-pollinated, has female fertility sufficient to achieve a grain set over about 30%.

10. The method of claim 1, wherein when self-pollinated, the female parent has a grain set which is less than about 5% of that for a selfed isogenic plant grown under the same conditions but without micronutrient deficiency, and when cross-pollinated, has female fertility sufficient to achieve a grain set over about 80%.

11. The method of claim 1 wherein biological availability of the micronutrient in the growth media is depressed by applying soil amendments.

12. The method of claim 1 further comprising testing a set of standard tolerant and sensitive check genotypes with known sterility/fertility responses in a set of growth media having concentrations of boron ranging from almost nil to sufficiency to determine the level of micronutrient deficiency to be used in a fertility-selective medium appropriate for the given environment and able to produce male sterility and female fertility in the tolerant and sensitive check genotypes.

13. The method of claim 12 wherein the plant is wheat and the set of standard check genotypes comprises a male fertile, tolerant line selected from the group consisting of Fang 60, Sonora 64, CMU-F2, CMU-F3, CMU-F4, CMU-F5, CMU-F6, CMU-F8, CMU-F9, CMU-F10, and CMU-F11; and a male sterile, female fertile, sensitive line selected from the group consisting of CMU-M1, CMU-M2, CMU-M9, CMU-M12, CMU-M21, BL1022, CMU-M23, CMU-M24, CMU-M27, RAC730, 84Z;1156, Kite, $U^2K212B$-4, Tatiara, Lin Calel, 82Y;1185, (YR10WARx)1/1, K11A-3, Sunelg, Bonza, Gamenya, Warrigal, QT5648, Aroona, Sundor, SUN276A, K1182, EL240, Bd9, Veery, Eradu, Kenya Farmer, ED089, Schombergk, BT Schombergk, Spear, Machete, Wilgoyne, Kite, BD231, ED135, Egret, Halberd, QT4546, QT4639, RAC710, SUN211A, SUN250c, Suneca, SW41, Tabuk, and WW1248.

14. A method according to claim 1, wherein the female plant and the male plant each has a different predetermined ability to transport a desired level of boron into the male reproductive organs, and wherein growing the female plant and growing the male plant comprises controlling male fertility by controlling the level of boron in the male reproductive organs.

15. The method of claim 14 further comprising determining a correlation between fertility and micronutrient content of the male reproductive organs by chemical analysis and observation of degrees of male sterility.

16. The method of claim 1 wherein male fertility is achieved by boron concentration in the anthers of about 11 mg B $kg^{-1}$ dry weight or more, and male sterility is achieved by boron concentration in the anthers at about 10 mg B $kg^{-1}$ dry weight or lower.

17. The method of claim 1 wherein about 50% male sterility, with Grain Set Index about 50% when self-fertilised, is achieved by boron concentration in the anthers at about 8 mg B $kg^{-1}$ dry weight or lower.

18. The method of claim 1 wherein complete male sterility, Grain Set Index about 0% when self-fertilised, is achieved by boron concentration in the anthers at about 6 mg B $kg^{-1}$ dry weight or lower.

19. The method of claim 1 wherein the wheat genotype is selected from Fang 60 and others with similar high boron uptake and transportation characteristics.

20. The method of claim 1 wherein the wheat genotype is selected from Gamenya, Tatiara, Kite, Machete, Spear, Bonza, Eradu, Warrigal, Wilgoyne, SW41 and others with similar low ability to take up and transport low levels of boron into their male reproductive organs.

21. A method for producing hybrid seeds comprising:
(a) providing a fertility-selective growth medium having a deficiency for a micronutrient wherein the micronutrient is boron;
(b) selecting from a plant species that is normally self-pollinating parents having different genotypes consisting of a female plant and a male plant, the plant being a monocotyledon,
    (i) the female plant having a phenotype of female fertility tolerance and male fertility sensitivity to the micronutrient deficiency, such that the plant does not produce normal pollen but has female fertility; and
    (ii) the male plant having a phenotype of male fertility tolerance to the micronutrient deficiency, and producing normal pollen;
(c) growing the female plant to sexual maturity in the fertility-selective growth medium to produce a plant having female fertility and male sterility;
(d) growing the male plant to sexual maturity to produce a plant having male fertility;
(e) cross-pollinating the female plant with pollen from the male plant to produce cross-fertilization;
(f) raising the female plant to produce hybrid seeds having genetic material from both parents; and
(g) harvesting the hybrid seeds.

22. An agricultural system comprising a combination of
(a) a fertility-selective growth medium having a deficiency for a micronutrient wherein the micronutrient is boron,
(b) grown together in the medium, a female specimen of a female plant variety and a male plant specimen of a male variety, both varieties being of a single plant species, the plant being a monocotyledon, the female plant specimen having female fertility but male sterility due to being grown in the medium, and the male plant producing normal pollen and having male fertility as grown in the medium.

23. The method of claim 21, wherein the plant is selected from the group consisting of wheat, barley, rice, rye, triticale, maize, sorghum, millet, and oats.

24. The method of claim 21, further comprising the step of stimulating the fertility of the female plant before cross-pollination by applying the micronutrient to the female plant without providing male fertility.

25. The method of claim 21 further comprising raising a hybrid plant from the hybrid seed.

26. The method of claim 21 further comprising raising the male and female together in the same growth medium and allowing cross-pollination to take place without manual assistance.

27. The method of claim 21 wherein biological availability of the micronutrient in the growth media is depressed by applying appropriate soil amendments.

28. A seed produced by the method of claim 21.

29. A plant produced from the seed of claim 28.

* * * * *